United States Patent
Amano et al.

(10) Patent No.: US 8,828,712 B2
(45) Date of Patent: Sep. 9, 2014

(54) GENETIC DETECTION AND DETERMINATION APPARATUS AND METHOD, GENE REACTOR, AND INCUBATOR

(75) Inventors: Masahiko Amano, Kisaradu (JP); Masaaki Chino, Kitakatsushika-gun (JP); Hiroyuki Kuroki, Kisaradu (JP); Makiko Dejima, Tokyo (JP); Tomoyuki Ozawa, Kisaradu (JP); Eiji Kawata, Kisaradu (JP); Ryoko Imagawa, Kisaradu (JP); Shuichi Akashi, Kisaradu (JP); Yusuke Nakamura, Tokyo (JP); Eiji Yamamoto, Iruma (JP); Katsuhiro Tomaru, Iruma (JP); Hajime Mogi, Iruma (JP)

(73) Assignees: Toppan Printing Co., Ltd., Tokyo (JP); Riken, Saitama (JP)

( * ) Notice: Subject to any disclaimer, the term of this patent is extended or adjusted under 35 U.S.C. 154(b) by 744 days.

(21) Appl. No.: 12/452,345

(22) PCT Filed: Jun. 27, 2008

(86) PCT No.: PCT/JP2008/061725
§ 371 (c)(1),
(2), (4) Date: Apr. 22, 2010

(87) PCT Pub. No.: WO2009/005001
PCT Pub. Date: Jan. 8, 2009

(65) Prior Publication Data
US 2010/0227383 A1 Sep. 9, 2010

(30) Foreign Application Priority Data

Jun. 29, 2007 (JP) ................. 2007-171867
Jul. 20, 2007 (JP) ................. 2007-189627

(51) Int. Cl.
| | | |
|---|---|---|
| C12M 1/00 | (2006.01) | |
| C12M 1/34 | (2006.01) | |
| C12M 1/36 | (2006.01) | |
| C12M 1/38 | (2006.01) | |
| C12M 3/00 | (2006.01) | |
| B01L 7/00 | (2006.01) | |
| B01L 3/00 | (2006.01) | |
| G01N 35/02 | (2006.01) | |
| G01N 35/00 | (2006.01) | |

(52) U.S. Cl.
CPC ............. *B01L 7/52* (2013.01); *G01N 35/026* (2013.01); *G01N 2035/00346* (2013.01); *B01L 2300/123* (2013.01); *B01L 2300/0829* (2013.01); *B01L 7/5255* (2013.01); *B01L 3/50851* (2013.01); *B01L 2200/0642* (2013.01); *B01L 3/505* (2013.01)
USPC ............. 435/287.2; 435/287.1; 435/286.1; 435/283.1; 435/288.4

(58) Field of Classification Search
USPC .................................... 435/283.1–309.4
See application file for complete search history.

(56) References Cited

U.S. PATENT DOCUMENTS

| | | | |
|---|---|---|---|
| 5,591,573 A * | 1/1997 | Whalen et al. .................. 435/5 |
| 6,597,450 B1 * | 7/2003 | Andrews et al. ............. 356/317 |
| 6,656,724 B1 | 12/2003 | Heimberg et al. | |
| 7,718,421 B2 * | 5/2010 | Chen et al. ................. 435/288.5 |
| 2004/0248146 A2 * | 12/2004 | Atwood et al. .................... 435/6 |
| 2007/0275455 A1 * | 11/2007 | Hung et al. ................. 435/287.1 |

FOREIGN PATENT DOCUMENTS

| | | |
|---|---|---|
| EP | 1 801 196 | 6/2007 |
| JP | 06-277036 | 10/1994 |
| JP | 2000-270837 | 10/2000 |
| JP | 2001-523823 | 12/2001 |
| JP | 2002-306154 | 10/2002 |
| JP | 2004-535200 | 11/2004 |
| JP | 2006-238759 | 9/2006 |
| JP | 2006-275820 | 10/2006 |
| JP | 2007-503217 | 2/2007 |
| JP | 2007-101347 | 4/2007 |
| JP | 2007-127622 | 5/2007 |

| WO | WO 03/007677 A2 | 1/2003 |
| WO | WO 2004/105947 | 12/2004 |
| WO | 2006/038643 | 4/2006 |

OTHER PUBLICATIONS

International Search Report issued on Sep. 16, 2009 in corresponding PCT Application No. PCT/JP2008/061725.
Japanese Office Action issued Dec. 21, 2012 for corresponding Japanese Application No. 2012-082488.
Japanese Office Action mailed Sep. 3, 2013 in corresponding Japanese Application No. 2012-082488.
Japanese Notice of Allowance mailed Apr. 22, 2014 in corresponding Japanese Application No. 2012-082488.

* cited by examiner

*Primary Examiner* — Nathan Bowers
*Assistant Examiner* — Lydia Edwards

(57) ABSTRACT

A genetic detection and determination apparatus which detects or determines genetic information, provided with a reaction container having a reaction vessel, including: a container set portion on which the reaction container is set; a moving mechanism which moves the container set portion along a track; a reaction vessel dividing portion which divides the reaction vessel into a plurality of reaction chambers by deforming the reaction vessel; a heating and cooling portion which heats and cools the reaction container; and a measuring portion which is movable above the container set portion in parallel to an upper surface of the reaction container provided on the container set portion and which measures a reaction within each of the reaction chambers.

24 Claims, 15 Drawing Sheets

GENETIC DETECTION AND DETERMINATION APPARATUS AND METHOD, GENE REACTOR, AND INCUBATOR

CROSS-REFERENCE TO RELATED APPLICATIONS

Priority is claimed on Japanese Patent Application No. 2007-171867, filed Jun. 29, 2007 and Japanese Patent Application No. 2007-189627, filed Jul. 20, 2007, the contents of which are incorporated herein by reference.

BACKGROUND

The present invention relates to a genetic determination apparatus, genetic reaction apparatus, and incubator.

BACKGROUND ART

In recent years, it has been discovered that individual information on, such as, metabolic rate or side effects of drugs can be obtained by investigating individual DNA polymorphism or the polymorphism of a nucleic acid base sequence. Thus, the need for genetic diagnosis is growing in clinical practice. Among various kinds of DNA polymorphism, detection of a single nucleotide polymorphism (SNP) is currently performed in many cases.

There are several typing methods for determining the SNP, such as the polymerase chain reaction (PCR), the invader assay, and the like, which are used independently or in combinations. The polymerase chain reaction (PCR) amplifies an area of a genetic material including the SNP using DNA polymerase, and the invader assay makes use of a structure-specific DNase.

As an example of a determination apparatus for genetic diagnosis performed in the above method, a determination apparatus having a configuration disclosed in Patent Document 1 is used. That is, a temperature control for amplification reaction of a genetic material and a temperature control for typing are performed by using two heat blocks. In addition, a sample after the amplification reaction is transferred by using a nozzle and is dispensed to a plurality of reaction portions where a probe for specifying the SNP is provided. Then, a measurement, such as a fluorescence measurement, is performed from below direction of the sample that is disposed in the reaction portion.

The polymerase chain reaction (PCR) is a widely used technique that amplifies DNA (genetic material) from a biological sample containing nucleic acid, such as DNA, obtained from blood or a sample, in a short time to thereby generate a large amount of DNA. This PCR technique denatures double-stranded DNA into single-stranded DNA at a high temperature and then lowers the temperature to anneal the primer to the single-stranded DNA. Then, new double-stranded DNA is synthesized by polymerases using the single-stranded DNA as a template. DNA is amplified by repeating these processes. An example of a thermal cycle repeats several tens of cycles, one cycle including approximately 1 minute at 95° C., several tens of seconds at 37° C., and several seconds to several minutes at 65° C.

In the PCR reaction, it is necessary to thus repeat heating and cooling of a sample. Accordingly, the whole reaction time is approximately determined by the number of repetitions (cycles) of heating and cooling required to reach a desired amount of genetic material amplification and the speed of heating and cooling to a target temperature required for the PCR reaction.

In addition, the type (kind) of the genetic material may be determined by fluorescence emission or electrochemical detection using reagents which work chemically, biologically, or electrically, after amplifying the genetic material.

A determination of the genetic material type may be performed at one constant temperature. In this case, the heating member used in the PCR reaction is also used for the determination of the genetic material type. As a result, since it becomes possible to reduce the number of components of an incubator, the apparatus can be made small.

In recent years, it has been discovered that information on the individual metabolic rate of a drug or side effects of a drug can be obtained by investigating individual DNA polymorphism or the polymorphism of a nucleic acid base sequence. For this reason, the need for quick genetic diagnosis (determination of genetic type) using a small apparatus is growing in clinical practice.

Examples of such an incubator include incubators that control the temperature of a reaction sample by moving a reaction block which holds the reaction sample between a heating block heated by a heater and a cooling block cooled by a cooling device, shortening the duration of a PCR reaction (refer to Patent Documents 2 and 3).

(Patent Document 1) Japanese Unexamined Patent Application, First Publication, 2006-275820.

(Patent Document 2) Japanese Unexamined Patent Application, First Publication, H6-277036

(Patent Document 3) Japanese Unexamined Patent Application, First Publication, 2000-270837

DISCLOSURE OF INVENTION

However, in the determination apparatus disclosed in Patent Document 1, the heat blocks are provided in two places and it is essential to prepare a dispensing mechanism for moving the nozzle. Accordingly, there is a problem that the apparatus needs to have at least a predetermined size.

Furthermore, when a sample is dispensed to reaction portions by using a nozzle, for example, dirt attached at the chip provided at the tip of the nozzle, or DNA in the air may be introduced into the reaction portion, that is, so called contamination may occur. This problem may also cause errors in the test results.

Furthermore, even if the dispensing mechanism is not used, human error, such as an operational mistake or contamination may occur when a reagent or a sample is dispensed by a manual operation on a reaction container, such as a DNA chip, set in the determination apparatus in order to perform a plurality of reactions.

The present invention was achieved in view of the above situation and has an object of providing a genetic detection and determination apparatus and a genetic reactor which are small and in which the occurrence of human errors or contamination are reduced.

In addition, there were the following problems in known incubators, such as the incubators disclosed in Patent Documents 2 and 3.

Such device would include, as essential components, a horizontal moving device and a vertical moving device. The horizontal moving device moves a reaction block in the horizontal direction, while the reaction block holding reaction samples. Thereby, the reaction block is moved to either one of a heating block or a cooling block. The vertical moving device moves the reaction block, after the horizontal movement, in the vertical direction, and thereby makes the reaction block either come in contact with or away from the heating block or the cooling block. For this reason, since the configuration of the apparatus is complicated, there has been a problem in that miniaturization is difficult.

In addition, a reaction sample absorbs or dissipates heat from the heating block or the cooling block through the reaction block. For this reason, a heating rate or a cooling rate is decreased by the heat capacity of the reaction block. As a result, since a PCR reaction time increases, there has been a problem in that it is difficult to perform genetic diagnosis quickly.

In addition, since the heating block and the cooling block are set beforehand to target temperatures, as the temperature of the reaction sample approaches the temperature of the heating block or the cooling block, the temperature difference between the sample and the heating block or the cooling block becomes small. For this reason, there has been a problem in that it is difficult to heat/cool the sample quickly.

In view of the above situation, a second object of the present invention is to provide an incubator which can be easily miniaturized with a simple configuration and can shorten the PCR reaction time by controlling the temperature of a reaction sample rapidly.

Means for Solving the Problem

In order to achieve the first object, the present invention adopts the following constitutions.

(1) A genetic detection and determination apparatus which detects or determines genetic information, provided with a reaction container having a reaction vessel, including: a container set portion on which the reaction container is set; a moving mechanism which moves the container set portion along a track; a reaction vessel dividing portion which divides the reaction vessel into a plurality of reaction chambers by deforming the reaction vessel; a heating and cooling portion which heats and cools the reaction container; and a measuring portion which is movable above the container set portion in parallel to an upper surface of the reaction container provided on the container set portion and which measures a reaction within each of the reaction chambers.

In the genetic detection and determination apparatus of the present invention, the reaction vessel is divided into the plurality of reaction chambers by the reaction vessel dividing portion. In addition, amplification and the typing reaction of DNA are performed in a reaction well by the heating and cooling portion. In addition, after the reaction is completed, a measurement is immediately performed above the container set portion by the measuring portion. Accordingly, a process of transferring a sample is not necessary.

(2) In the genetic detection and determination apparatus described above, the heating and cooling portion may perform at least one of heating and cooling of the reaction container from at least one of a bottom surface and an upper surface of the reaction container.

In this case, since an operation space of the heating and cooling portion is reduced, the apparatus can be made smaller.

(3) Furthermore, in the genetic detection and determination apparatus described above, the reaction vessel dividing portion may divide the reaction vessel by plastic deformation.

In this case, the reaction vessel can be reliably divided to make respective reaction chambers independent of each other and the process can proceed to the next process in the state.

(4) Furthermore, the genetic detection and determination apparatus described above may further include: a determining portion which detects or determines the genetic information based on a measurement value of the measuring portion and searches and acquires related information relevant to a determination result from a database; and a display portion that displays the determination result of the determining portion and the related information.

In this case, the determination result can be immediately used for daily clinical activity.

(5) Furthermore, the genetic detection and determination apparatus described above may further include a reader portion which reads information from an information recording portion which is included in the reaction container.

In this case, the type of a sample within the reaction container is appropriately identified. As a result, the measurement result can be processed more suitably.

Furthermore, in order to achieve the first object, the present invention adopts the following.

(6) A genetic detection and determination method of detecting or determining a predetermined genetic information using a reaction container having a reaction vessel, including: adding a sample containing a genetic material in the reaction vessel of the reaction container; executing a reaction vessel dividing process which forms a plurality of reaction chambers in the reaction container by deforming the reaction vessel; executing an amplification reaction process which performs an amplification and a typing reaction of the genetic information within the sample by performing at least one of heating and cooling of the reaction container from at least one of a bottom surface and an upper surface of the reaction container; executing a measuring process which measures a result of the reaction within each of the reaction chambers during or after the amplification reaction process; and detecting or determining the genetic information based on a measurement value obtained in the measuring process.

According to the genetic detection and determination method, since the reaction vessel is shaped into the plurality of reaction chambers in the reaction vessel dividing process, the amplification reaction process and the measuring process are performed without a need of dispensing.

Furthermore, in order to achieve the first object, the present invention adopts the following configuration.

(7) A genetic reactor which detects or determines genetic information, provided with a reaction container having a reaction vessel, including: a container set portion on which the reaction container is set; a moving mechanism which moves the container set portion along a track; a reaction vessel dividing portion which divides the reaction vessel into a plurality of reaction chambers by deforming the reaction vessel; and a heating and cooling portion which heats and cools the reaction container.

In the genetic reactor of the present invention, the reaction vessel is divided into the plurality of reaction chambers by the reaction vessel dividing portion. In addition, amplification and the typing reaction of DNA are performed in a reaction well by the heating and cooling portion. Accordingly, a process of transferring a sample is not necessary.

Furthermore, in order to achieve the second object, the present invention adopts the following configuration.

(8) An incubator including: a container in which a reaction sample is accommodated; a heat-conductive heat transfer block on which the container is set and which holds the container; a heater which is in contact with the heat transfer block and heats the heat transfer block; a cooling device which is movable between a contact position being in contact with the heater and a distant position separated from the heater, and which comes in contact with the heater at the contact position to cool the heat transfer block; and a moving device which moves the cooling device to the contact position and the distant position.

(9) Furthermore, the incubator described above may have the following configuration: the heater is in contact with a bottom surface of the heat transfer block, the cooling device is in contact with a bottom surface of the heater at the contact position, and the moving device supports the cooling device from at least one of the downward and lateral directions thereof.

(10) Furthermore, the incubator described above may have the following configuration: the moving device includes an air cylinder.

(11) Furthermore, the incubator described above may have the following configuration: the moving device includes an electromagnetic actuator.

(12) Furthermore, the incubator described above may have the following configuration: the heat transfer block includes a heat-conductive material.

(13) Furthermore, the incubator described above may have the following configuration: the heater includes a ceramic material with high thermal conductivity.

(14) Furthermore, the incubator described above may have the following configuration: the ceramic material contains aluminum nitride, aluminum oxide, silicon carbide, or silicon nitride.

(15) Furthermore, the incubator described above may have the following configuration: the cooling device has a contact surface being in contact with the heater and a thermally conductive sheet which is provided at the contact surface.

(16) Furthermore, the incubator described above may have the following configuration: the cooling device includes a heat sink.

(17) Furthermore, the incubator described above may have the following configuration: the heat sink has a pipeline through which a fluid flows and the heat sink is cooled by cooling water which flows to circulate through the pipeline.

(18) Furthermore, the incubator described above may have the following configuration: the heat sink has a pipeline through which a fluid flows, and the heat sink is cooled by a refrigerant which flows to circulate through the pipeline and has a lower boiling point than a predetermined cooling temperature.

(19) Furthermore, the incubator described above may have the following configuration: the cooling device has a heat sink and a fan for cooling the heat sink.

(20) Furthermore, the incubator described above may have the following configuration: the cooling device includes: a metal block which transfers heat to the heater; a Peltier element which has a heat absorbing surface for absorbing heat and a heat dissipating surface for dissipating heat, the heat absorbing surface being in contact with the metal block; a heat sink being in contact with the heat dissipating surface of the Peltier element; and a fan which cools the heat sink.

(21) Furthermore, the incubator described above may have the following configuration: the metal block includes a heat-conductive material.

(22) Furthermore, the incubator described above may have the following configuration: the cooling device includes: a Peltier element which has a heat absorbing surface for absorbing heat and a heat dissipating surface for dissipating heat; a heat sink being in contact with the heat dissipating surface of the Peltier element; and a fan which cools the heat sink.

Furthermore, in order to achieve the first object, the present invention adopts the following configuration.

(23) A genetic detection and determination apparatus which detects or determines genetic information provided with a reaction container having a reaction vessel, including: the aforementioned incubator; a container set portion on which the reaction container is set; a moving mechanism which moves the container set portion along a track; a reaction vessel dividing portion which divides the reaction vessel into a plurality of reaction chambers by deforming the reaction vessel; and a measuring portion which is movable above the container set portion in parallel to an upper surface of the reaction container provided on the container set portion and which measures reaction within each of the reaction chambers.

Effects of the Invention

According to the genetic detection and determination apparatus of the present invention, the genetic detection and determination apparatus and the genetic reactor which are small and in which human error and contamination rarely occurs can be provided.

In addition, according to the genetic detection determination method of the present invention, the genetic determination can be performed while suppressing human error or contamination.

Moreover, according to the incubator of the present invention, in the case of heating a reaction sample, the heat transfer block that holds the container in which the reaction sample is accommodated is quickly heated by the heater provided to be in contact with the heat transfer block. In this case, the cooling device is positioned to be separated from the heater by the moving device. On the other hand, in the case of cooling a reaction sample, the cooling device is immediately moved to the contact position being in contact with the heater by the moving device such that the heat transfer block is immediately cooled through the heater by the cooling device. Thus, the temperature of the reaction sample can be controlled rapidly by quickly heating or cooling the reaction sample.

In addition, only the moving device which moves the cooling device to the contact position and the distant position is a movable member. Accordingly, it is possible to make the configuration of the apparatus simple and it becomes easy to make the apparatus small.

DESCRIPTION OF REFERENCE NUMERALS AND SIGNS

Figure 1:
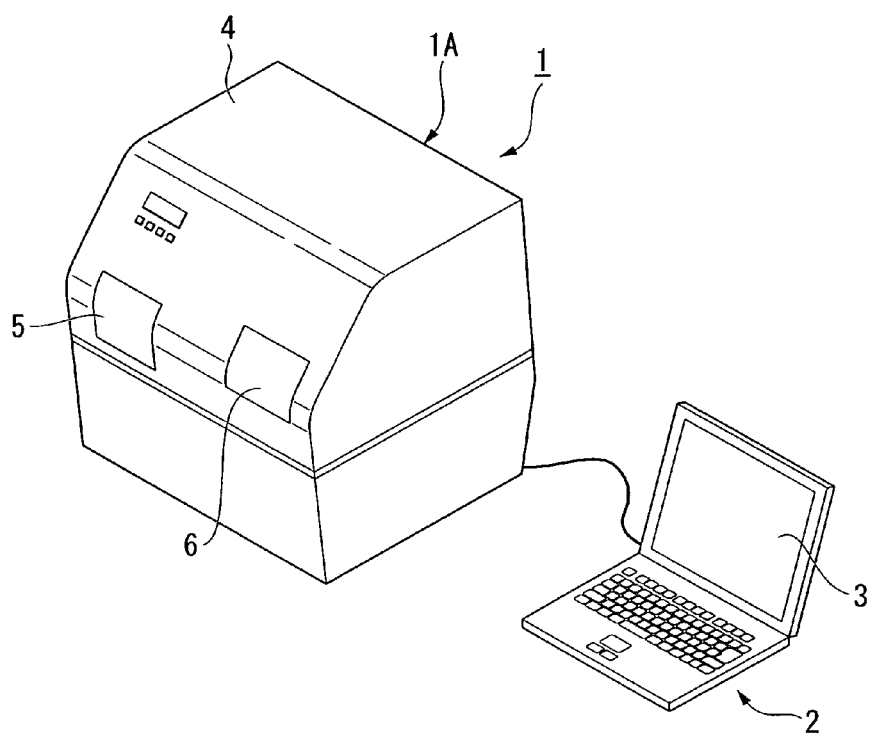
FIG. 1 is a perspective view illustrating a genetic detection and determination apparatus according to a first embodiment of the present invention.

1: genetic detection and determination apparatus
7: movable board (container set portion)
8: reaction vessel dividing portion
9: temperature control portion (heating and cooling portion)
10: measuring portion
11: moving mechanism
12: rail
23: determining portion
24: reader portion
100: reaction container
102: reaction vessel
105: reaction chamber
210: DNA chip
212: press
220: heat transfer block
230: heater
240: cooling device
260: moving device
270: chip base

BEST MODE FOR CARRYING OUT THE INVENTION

Hereinafter, a genetic detection and determination apparatus (hereinafter, referred to as a 'determination apparatus') according to a first embodiment of the present invention will be described with reference to FIGS. 1 to 9.

FIG. 1 is a perspective view illustrating a determination apparatus 1. The determination apparatus 1 is configured to include a determination apparatus body 1A and a personal computer 2 connected to the determination apparatus body 1A. The personal computer 2 has a display portion 3, such as a display. An upper portion of the determination apparatus body 1A is covered with a cover 4 in order to prevent contamination and the like. A sample load door 5, which is opened and closed when setting a reaction container to be described later, and an apparatus display portion 6, which displays a state of the determination apparatus 1, are provided on a front part of the cover 4. Various states and information, such as occurrence of abnormal status in the determination apparatus 1, or a currently performed process, are displayed on the apparatus display portion 6.

Figure 2:
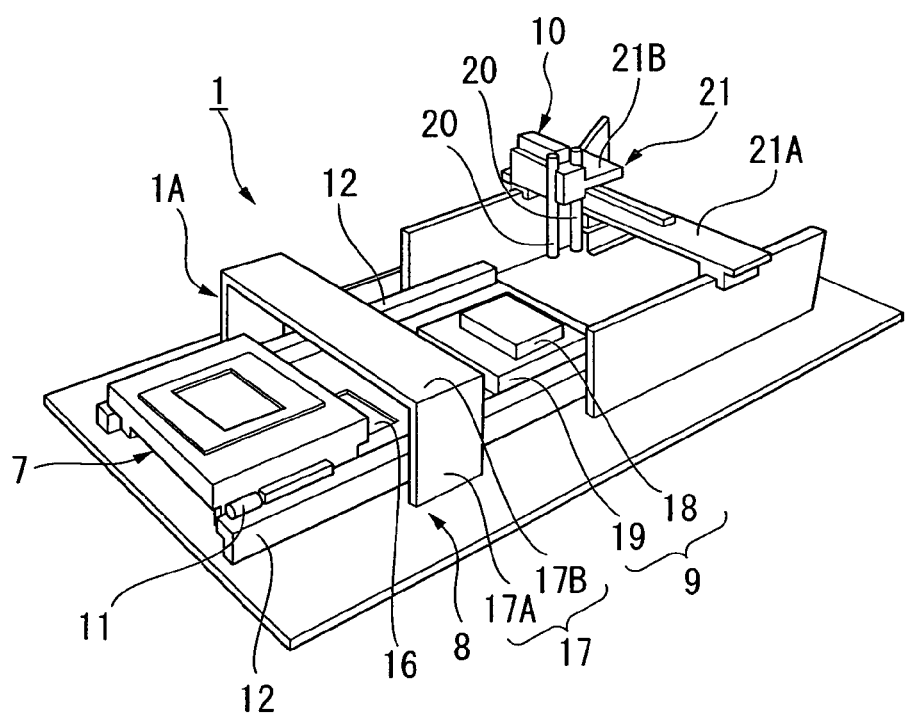
FIG. 2 is a perspective view illustrating a state in which a cover of the genetic detection and determination apparatus is removed.

FIG. 2 is a perspective view illustrating a state in which the cover 4 of the determination apparatus body 1A is removed. The determination apparatus 1 includes a movable board (container set portion) 7 on which a reaction container is set, a reaction vessel dividing portion 8 which divides a reaction vessel of a corresponding reaction container to be described later into a plurality of reaction chambers, a temperature control portion (heating and cooling portion) 9 which heats and cools the reaction container, and a measuring portion 10 which measures the reaction of the reaction container.

The movable board 7 is configured to move above the reaction vessel dividing portion 8 and the temperature control portion 9 along a rail 12 provided on an upper surface of the determination apparatus 1 by a moving mechanism 11 having a known configuration, such as a stepping motor or a servo motor. In the present embodiment, the rail 12 is provided as a straight line extending backward from the vicinity of the sample load door 5.

In addition to the above configuration, the configuration of a known moving mechanism, such as the combination of a stepping motor and a belt or a configuration in which the rail 12 and the movable board 7 are moved by using a magnetic force or the like, may be appropriately selected as the configuration of the moving mechanism 11. In the present embodiment, the moving mechanism 11 of the determination apparatus 1 is configured by using a stepping motor and an endless belt.

Figure 3A:
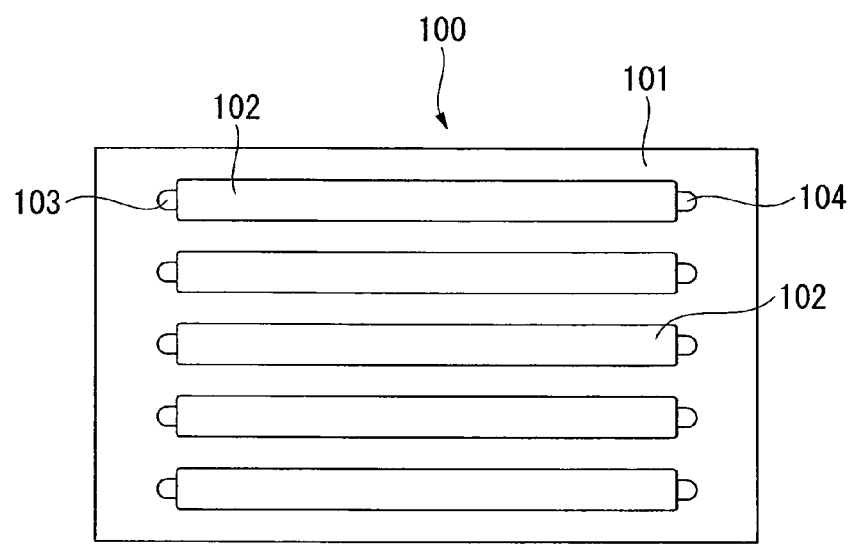
FIG. 3A is a plan view illustrating an example of a reaction container used in the genetic detection and determination apparatus.
Figure 3B:
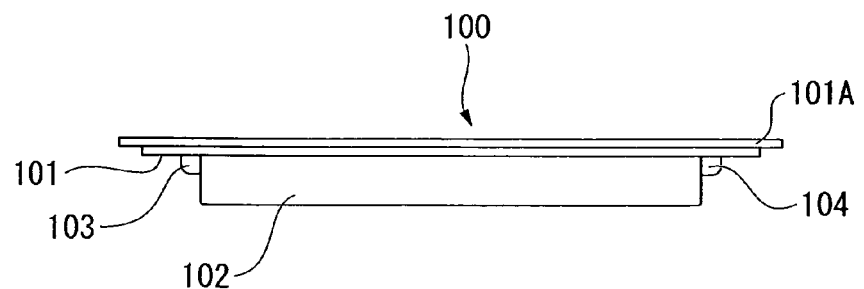
FIG. 3B is a front view illustrating an example of a reaction container used in the genetic detection and determination apparatus.

FIG. 3A is a plan view illustrating an example of a reaction container set in the determination apparatus 1, and FIG. 3B is a front view thereof. In the reaction container 100, a plurality of grooved reaction vessels 102 are disposed on a base board 101 formed of a resin, or the like, so as to be aligned approximately in parallel to each other. The required amount of reagent used for a PCR reaction and typing reaction is filled beforehand in each reaction vessel 102. In addition, the upper surface is covered with an upper surface cover 101A formed of a resin or the like, in order to prevent contamination. In addition, a predetermined space is secured so that a sample containing a genetic material can be added as described above.

In addition, an enzyme may be contained in the reagent. These reagents may be provided in a desired state according to a request of placement to a reaction vessel, such as a dried state (including freeze drying, heat drying, and the like), a gel state, or a powder state. In addition, these reagents may be placed in a state sealed with wax, for example.

As shown in FIG. 3A, an inlet 103 and an aeration hole 104 are provided in the upper surface cover 101A at both ends of each reaction vessel 102. When a sample is injected through the inlet 103 by a syringe, or the like, the air within each reaction vessel 102 escapes from the aeration hole 104. As a result, the sample is placed in each reaction vessel 102.

The upper surface cover 101A of the reaction container 100 is preferably formed of a material which is low in self-fluorescence and through which excitation light and fluorescent light are transmitted. The base board 101 and the reaction vessel 102 are preferably formed of a material through which excitation light and fluorescent light are not transmitted and which has good thermal conductivity. Instead of selecting the material, it may also be possible to prevent excitation light and fluorescent light from being transmitted by coloring the bottom surface. Furthermore, it is preferable to form the reaction container 100 with a material which is flexible to some extent so that a large deformation or crack does not occur in a reaction vessel division process to be described later.

Figure 4:
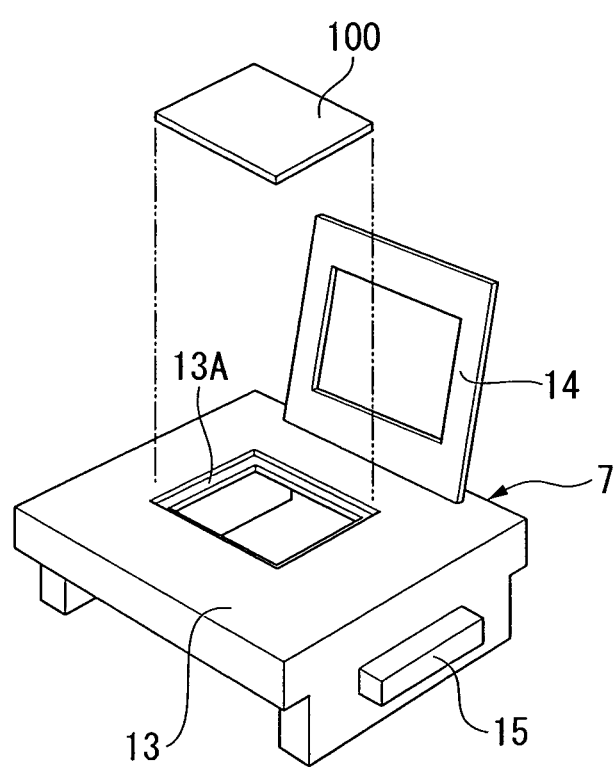
FIG. 4 is a perspective view illustrating a movable board of the genetic detection and determination apparatus.

FIG. 4 is a perspective view illustrating the movable board 7. The movable board 7 has a frame-shaped set portion 13 on which the reaction container 100 is set, a container cover 14 for fixing the reaction container 100 set on the set portion 13, and a conveying portion 15 provided on the rail 12.

The set portion 13 has a holding portion 13A extending horizontally within the frame and is fixed to the movable board 7 when an outer periphery portion of the reaction container 100 is held on the holding portion 13A. Accordingly, a bottom surface of the reaction container 100 is not covered with the movable board 7, but the reaction container 100 is set and fixed in a state where a bottom surface of each reaction vessel 102 is exposed.

The container cover 14 is fixed to the set portion 13 by a hinge, or the like, so as to be freely opened and closed and fixes the reaction container 100 set on the set portion 13 from above. The movable board 7 moves along the rail 12 in a state of being placed on a plurality of the rails 12 as the conveying portion 15 on the rail 12 moves by the moving mechanism 11.

Referring back to FIG. 2, the reaction vessel dividing portion 8 is provided between the rails 12, that is, a track along which the movable board 7 moves. The reaction vessel dividing portion 8 is configured to include a pressing block 16 capable of moving in a vertical direction and an arch portion 17 provided above the pressing block 16.

A plurality of protruding portions that protrude toward a portion are provided at the pressing block 16 such that they position immediately below each reaction vessel 102 when the reaction container 100 on the movable board 7 is located immediately above the pressing block 16. The protruding portion divides the reaction vessel 102 into a plurality of reaction chambers by deforming the reaction vessel 102 when the pressing block 16 goes up.

The arch portion 17 is configured to include a vertical section 17A extending upward from left and right sides of the rails 12 and a top plate 17B provided to bridge upper ends of the vertical section 17A. Since the area of the top plate 17B is set to a size sufficient to cover the entire reaction container 100 set on the movable board 7, the top plate 17B functions as a press which comes in contact with the pressing block 16 when the pressing block 16 goes up.

A protruding portion, which has about the same area as an opening of the set portion 13 of the movable board 7 on which the reaction container 100 is set and which protrudes toward the reaction container 100, may be provided at the top plate 17B. In this manner, it is possible to hold and press the reaction container 100 more reliably.

The temperature control portion 9 including a heating portion 18 may be formed: by using any of various kinds of heaters, such as an electric heater, a ceramic heater, a laser, a halogen lamp, an infrared heater, a microwave heater, a hot air heater, or an induction heating (IH) heater; and a cooling portion 19 which is provided below the heating portion 18 and is formed by using an electric fan, a heat sink, a cold air cooler, or the like. If necessary, the heating portion 18 and the cooling portion 19 may be constituted by using a Peltier element.

The temperature control portion 9 is provided between the rails 12 spaced apart from the reaction vessel dividing portion 8 by a predetermined distance, that is, on the track of the movable board 7 so as to be movable in the vertical direction. In addition, the temperature control portion 9 goes up from the movable board 7, which has moved above the temperature control portion 9 and stopped, coming in contact with the bottom surface of the reaction container 100, that is, the bottom surface of each reaction vessel 102. The temperature control portion 9 heats or cools the reaction container 100 by using the heating portion 18 or the cooling portion 19 and realizes a temperature cycle required for the PCR or performs holding (temperature holding) of a predetermined temperature required for the typing reaction.

If necessary, for example, a metallic foil or silicon grease may be provided between the temperature control portion 9 and the reaction container 100 in order to improve thermal conductivity. The temperature control of the temperature control portion 9 is performed by a control portion to be described later.

The temperature control portion 9 and the reaction container may be reliably brought into contact with each other by providing one more arch portion 17 in the temperature control portion 9 and pressing the movable board 7 or the reaction container 100 against the temperature control portion 9 and the arch portion 17.

In addition, it may also be possible to adopt a configuration in which the arch portion 17 is provided in one place and the pressing block 16 or the temperature control portion 9 moves.

In addition, the arch portion 17 may also be provided to cover the temperature control portion 9 and the pressing block 16.

The measuring portion 10 is configured to include an emission detecting portion 20 which performs the introduction of excitation light and the measurement of fluorescent light, and a measuring portion moving mechanism 21 which moves the emission detecting portion 20.

The emission detecting portion 20 is formed by tying several optical fibers for excitation light (not shown) which serve to introduce excitation light and several optical fibers for detection (not shown) which serve to measure (detect) fluorescent light generated by excitation light in a group. In the determination apparatus 1, the emission detecting portion 20 is provided in two places. The number of the emission detecting portions 20 may be appropriately changed according to the speed required for measurement of light.

A known mechanism, such as a light emitting diode (LED) or a laser diode, may be suitably selected and used as a light source of excitation light. In the determination apparatus 1 according to the present embodiment, an LED having a wavelength range of, for example, 400 to 600 nm is used.

In addition, a wavelength required for fluorescent dye (fluorescent material) of an object to be measured may be appropriately selected as the wavelength of excitation light.

A photo multiplier tube (PMT; not shown) which measures the fluorescence intensity by converting condensed fluorescent light into a voltage or a current is connected to the optical fibers for detection. In the present embodiment, the emission detecting portion 20 has two PMTs having wavelength ranges of about 530 and 610 nm. The number of PMTs may be appropriately changed according to the number of wavelengths to be measured. Alternatively, for example, a photodiode or a photoelectric conversion element using a CCD may also be used instead of the PMT.

In addition, the measured wavelength of the emission detecting portion 20 may also be appropriately changed according to the fluorescent dye (fluorescent material) of an object to be measured.

In addition, one or more of filters or lenses for condensing may be provided in the emission detecting portion 20 as needed.

Moreover, the emission detecting portion 20 may be configured to detect chemiluminescence, bioluminescence, phosphorescence, or the like, instead of fluorescence. In this case, when a light source for excitation is not necessary for the object to be detected, the configuration may be appropriately changed.

The measuring portion moving mechanism 21 is formed by using a known motor or the like, and the moving mechanism 11 which moves the movable board 7. The measuring portion moving mechanism 21 is formed by combining an X-axis moving portion 21A, which moves the emission detecting portion 20 in the X-axis direction (forward and backward direction of the movable board 7), and a Y-axis moving portion 21B, which moves the emission detecting portion 20 in the Y-axis direction (width direction of the rail 12). Thus, the emission detecting portion 20 can move above each reaction vessel 102 in parallel with an upper surface of the reaction container 100 on the movable board 7 which stops above the temperature control portion 9.

The measuring portion moving mechanism 21 may be configured to further include a mechanism, which moves the emission detecting portion 20 in a Z-axis direction (vertical direction), so that fine adjustment of the position of the emission detecting portion 20 can be performed as needed.

Figure 5:
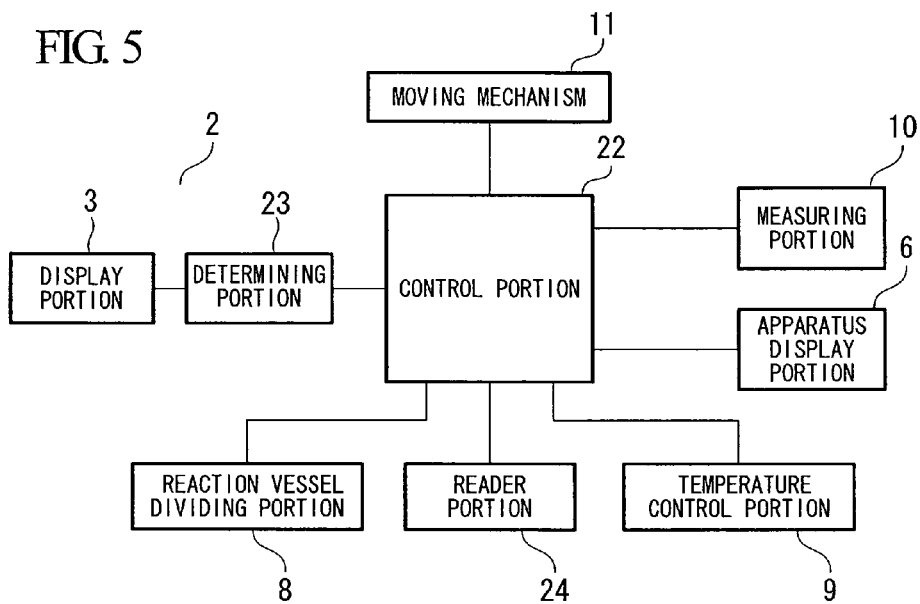
FIG. 5 is a block diagram illustrating the configuration of the genetic detection and determination apparatus.

FIG. 5 is a block diagram illustrating an example of the connection of the respective portions of the determination apparatus 1. As shown in FIG. 5, the apparatus display portion 6, the moving mechanism 11, the reaction vessel dividing portion 8, the temperature control portion 9, and the measuring portion 10 are connected to a control portion 22 which controls the entire determination apparatus 1. In addition, the control portion 22 is also connected to a determining portion 23 that makes a determination based on the fluorescence intensity acquired by the measuring portion 10 and a reader portion 24 which reads information on the reaction container 100.

The control portion 22 controls the operation of each of the mechanisms connected as described above and a PCR temperature cycle or a heating temperature in the temperature control portion 9. The control portion 22 may be provided inside the determination apparatus body 1A or may be provided outside the determination apparatus body 1A. In the case where the control portion 22 is provided inside the determination apparatus body 1A, the control portion 22 may be provided in the form of a micro CPU, a ROM, a RAM, a programmable logic controller (PLC), and the like. In the case where the control portion 22 is provided outside the determination apparatus body 1A, the control portion 22 may be stored as a control program, such as software, in the personal computer 2 connected to the determination apparatus body 1A, or the like. In addition, the control portion 22 may be separately provided inside and outside the determination apparatus body 1A.

The determining portion 23 is stored in the personal computer 2 having the display portion 3. The determining portion 23 is configured to include determination parameters, algorithms, and a determination database corresponding to genetic polymorphism of an object to be measured. The determining portion 23 performs a predetermined determination on whether a measured SNP part is of a homogeneous type or a heterogeneous type based on a value of the fluorescence intensity obtained in the emission detecting portion 20 of the measuring portion 10 and the above-described determination parameter and displays the result on the display portion 3.

In addition, the above database may not be included in the determining portion 23. For example, a database of another terminal may be searched through the Internet, or a plurality of sites on the Internet may be referenced.

In addition, information that a medical doctor needs to take into consideration in an actual prescription, such as; information on disease cases or medicine prescription regarding the measured SNP part; package inserts and interaction information of related medicines; and urgent safety information (doctor letter), may also be included as information on the database. In addition, such information may be displayed on the display portion 3 together with a determination result.

The reader portion 24 reads various kinds of information, such as a measurement object of a reaction container and a sample number, from an information recording portion provided in the reaction container 100. As the information recording section, a two-dimensional barcode, an RFID (radio frequency identification), an IC tip, an IC tag, or an antenna may be used. Various kinds of read information are displayed on the display portion 3 together with a determination result or are used for the arrangement of data, such as the determination result. Various kinds of information may be displayed on the apparatus display portion 6 as necessary.

An operation in using the determination apparatus 1 configured as described above will be described below.

Figure 6:
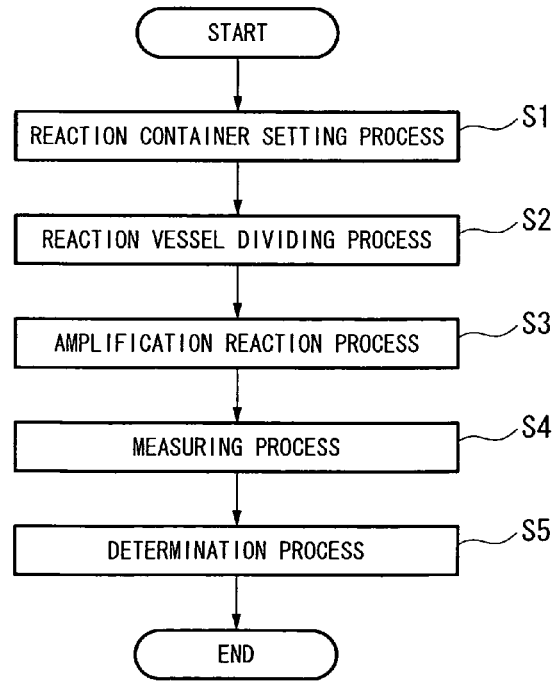
FIG. 6 is a flow chart illustrating procedures of genetic diagnosis using the determination apparatus.

FIG. 6 is a flow chart illustrating procedures of genetic diagnosis using the determination apparatus 1. First, in a reaction container setting process of step S1, the reaction container 100 into which a sample is injected is set on the set portion 13 of the movable board 7 by opening the sample load door 5 and the container cover 14 is mounted. The sample load door 5 is closed after mounting the container cover.

The injection of a sample into the reaction container 100 is performed by injecting a DNA sample obtained by nucleic acid extraction, for example, by applying pressure from the inlet 103 of the reaction container 100 by a syringe or the like. The injected sample is disposed approximately homogeneously in each reaction vessel 102 and is mixed with a reagent in the reaction vessel.

In addition, in the case when the reaction container has a nucleic acid extracting function, a process, such as nucleic acid extraction, may be omitted.

The movable board 7 on which the reaction container 100 is set moves above the reaction vessel dividing portion 8 along the rails 12 and stops by the moving mechanism 11.

Figure 7A:
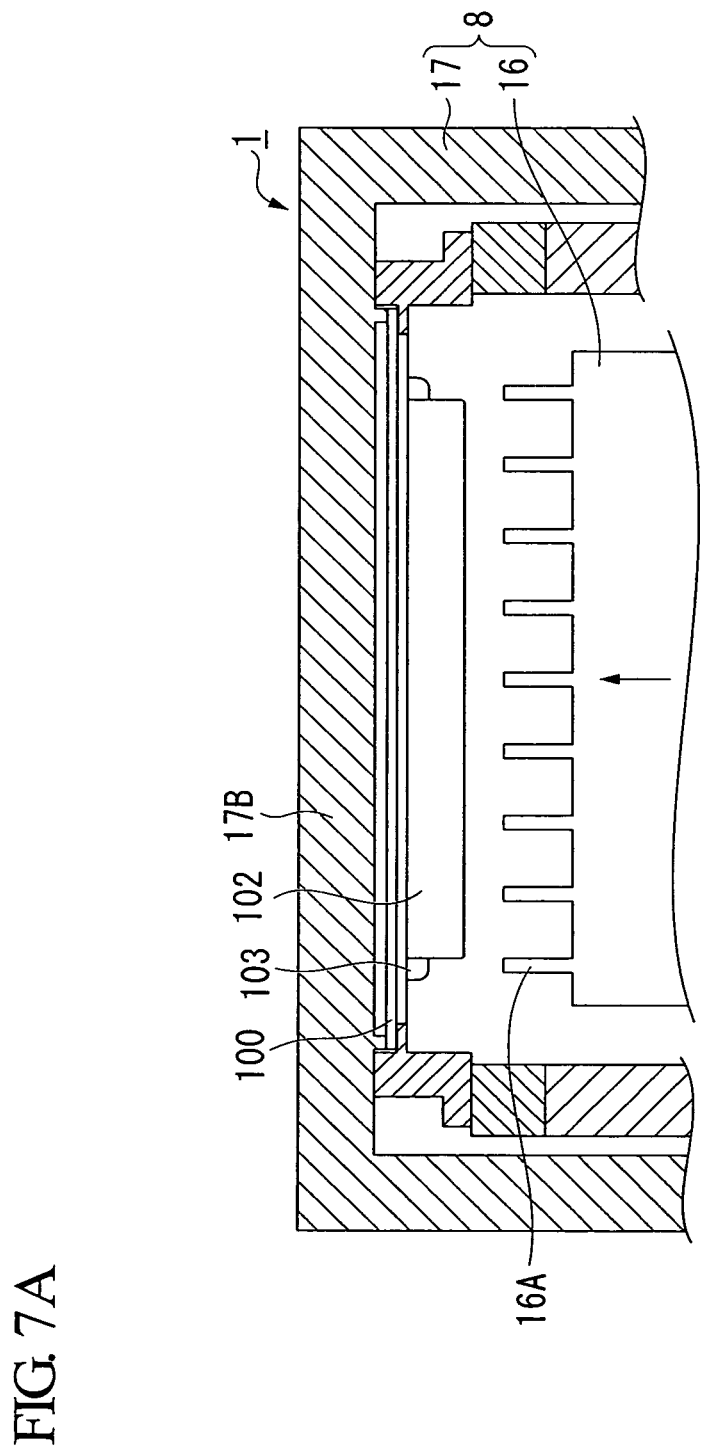
FIG. 7A illustrates an operation of a sealing portion of the genetic detection and determination apparatus.

Then, in a reaction vessel dividing process of step S2, the pressing block 16 of the reaction vessel dividing portion 8 goes up to come in contact with a bottom surface of the reaction container 100, as shown in FIG. 7A. The pressing block 16 further goes up to make the reaction container 100 come in contact with the arch portion 17 with a predetermined pressure.

Figure 7B:
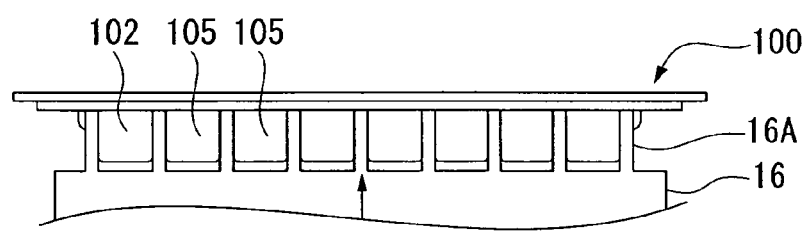
FIG. 7B illustrates an operation of the sealing portion of the genetic detection and determination apparatus.

Each reaction vessel 102 is inserted between a plurality of protruding portions 16A on the pressing block 16 and the top plate 17B of the arch portion 17 and plastically deforms due to pressure as shown in FIG. 7B. Depending on the material of the reaction container 100, the reaction chamber 105 may also be formed without the plastic deformation.

As a result, each reaction vessel 102 is divided into the plurality of independent reaction chambers 105, such that a reaction can be performed in each reaction chamber.

Figure 7C:
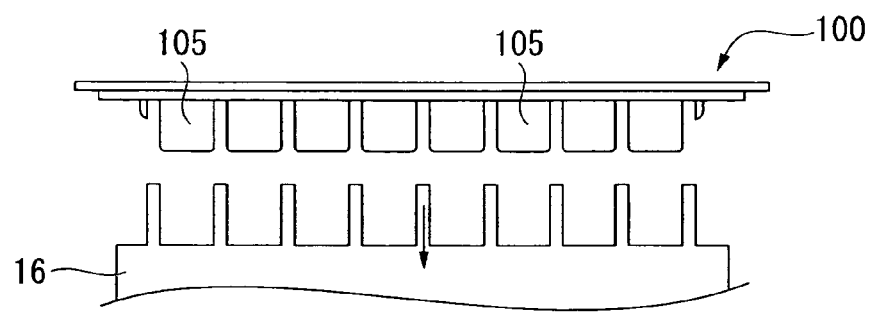
FIG. 7C illustrates an operation of the sealing portion of the genetic detection and determination apparatus.

After forming the reaction chamber 105, the pressing block 16 goes down to return to a predetermined position as shown in FIG. 7C, and the movable board 7 on which the reaction container 100 is set moves above the temperature control portion 9 along the rails 12 and stops by way of the moving mechanism 11.

Then, in an amplification reaction process of step S3, amplification of DNA using the PCR and typing reaction using the invader assay are performed by controlling the temperature.

Figure 8:
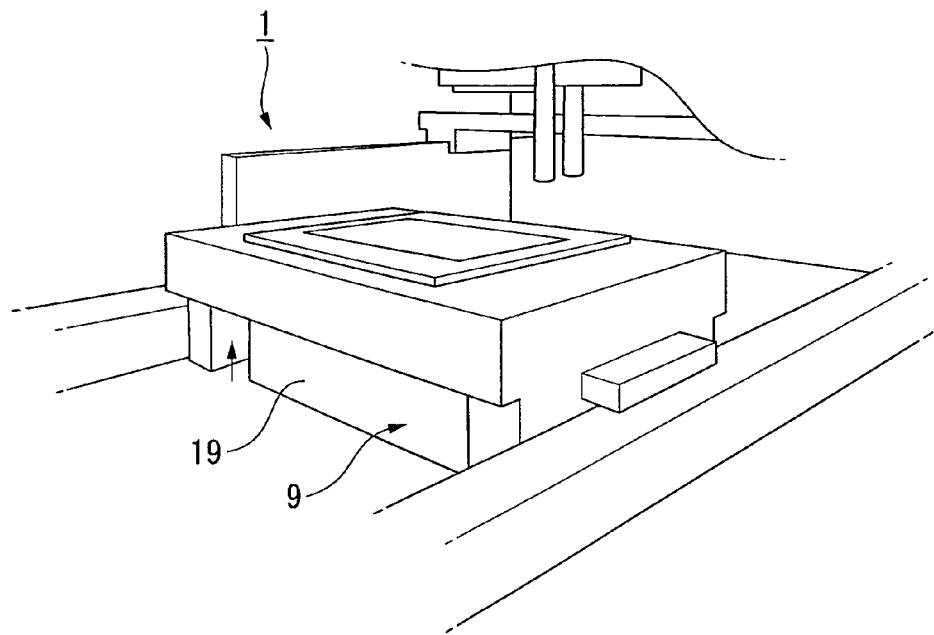
FIG. 8 illustrates an operation of a temperature control portion of the genetic detection and determination apparatus.

First, as shown in FIG. 8, the temperature control portion 9 goes up to come in contact with the bottom surface of the reaction container 100 (not shown). The temperature control portion 9 heats or cools the reaction container 100 to a predetermined temperature based on a control of the control portion 22. Heating is performed by supplying power to the heating portion 18 (not shown), and cooling is performed by stopping the power supply to the heating portion 18 or changing a power supply condition in order to dissipate the heat through the cooling portion 19.

In addition, in the case of using a refrigerant which will be described later, the temperature is controlled by stopping supply of the refrigerant or changing the amount of refrigerant supplied instead of the power supply. This adjustment amount is separately stored in the control portion 22 beforehand.

Then, the solution within each reaction chamber 105 of the reaction container 100 is heated a multiple number of times in a predetermined temperature cycle, for example, 30 cycles such that the PCR reaction progresses and is then held at a predetermined temperature, for example, about 60° C., for about two minutes such that the typing reaction progresses. After the typing reaction is completed, the temperature control portion 9 goes down and stops.

As methods of amplification and the typing reaction, known methods, such as an ICAN method, a UCAN method, and a LAMP (loop-mediated isothermal amplification) method may also be used in addition to the above-described methods.

In the measuring process of step S4, the fluorescence intensity corresponding to an SNP part is measured by irradiating excitation light from the emission detecting portion 20 onto the sample after the typing reaction in each reaction chamber 105.

Figure 9:
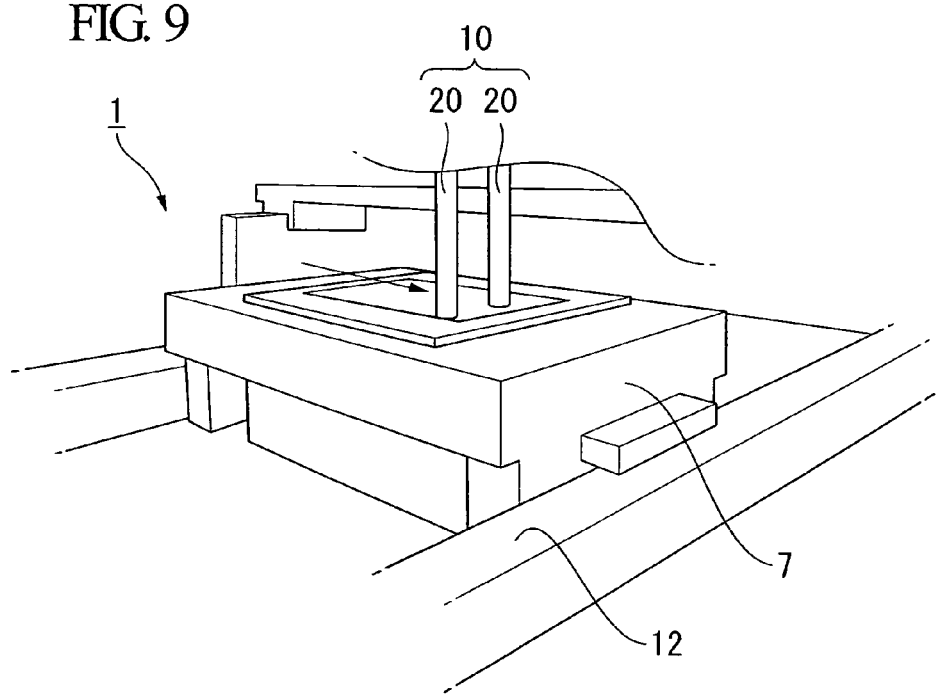
FIG. 9 illustrates an operation of a measuring portion of the genetic detection and determination apparatus.

Specifically, as shown in FIG. 9, the fluorescence measurement is performed by moving the measuring portion 10 while scanning an upper portion of each reaction chamber 105 (not shown) of the reaction container 100 (not shown) and irradiating excitation light by the emission detecting portion 20. A measurement result acquired by the emission detecting portion 20 is transmitted to the determining portion 23.

Measurement data (measurement result) may be collectively transmitted to the determining portion 23 after measurement, or the measurement data may be transmitted in a sequential manner. In the case of storing data before collective transmission is performed, a storage medium, such as a memory unit, may be provided in the determination apparatus 1. Connection between the determination apparatus body 1A and the personal computer 2 may be freely selected, that is, may be wirelessly or with a cable, or the like. However, the connection between the determination apparatus body 1A and the personal computer 2 is preferably made with a cable in terms of stability of data transmission.

As a method of transmitting a measurement result from the determination apparatus body 1A to the outside (including the personal computer 2), various kinds of external storage media including a USB (universal serial bus) memory unit, a hard disk, a CD-ROM, and a DVD-ROM may be used in addition to those described above.

After measurement in all reaction chambers 105 is completed, the measuring portion 10 returns to the original position and stops, proceeding to the determination process of step S5.

In addition, the measuring process may be performed before the typing reaction in the amplification reaction process, or may start almost simultaneously with the start such that the above-mentioned scanning is performed a multiple number of times until the typing reaction sufficiently progresses.

Alternatively, the measuring process may be performed after the PCR reaction is completed and storage at a predetermined temperature is maintained during a predetermined time.

That is, it is not necessarily meant that the respective processes shown in FIG. 6 are independently performed and in the order shown in FIG. 6, but cases where the plurality of processes are performed repeatedly or overlapped in a time-sequential manner are also included.

In the above case, the time in which the PCR reaction and the typing reaction are completed is separately measured for each object to be measured and is input to the control portion 22 beforehand.

In the determination process, a value of the fluorescence intensity acquired by the measuring portion 10 is determined based on a determination algorithm suitable for an SNP to be measured by the determining portion 23. A determination result indicating, for example, whether the SNP part is of a homogeneous type or a heterogeneous type is displayed on the display portion 3 of the personal computer 2. In this case, if necessary, it may be possible to search the related information from a database present inside or outside the determination apparatus 1 and to display the information on the display portion 3 together with the determination result.

After the determination process is completed, the movable board 7 returns toward the sample load door 5 along the rails 12. The movable board 7 moves up to the position, at which the movable board 7 has been placed in step S1, and stops. In this way, a series of processes are completed.

In the determination apparatus 1 according to the present embodiment, the reaction vessel 102 of the reaction container 100 plastically deforms by the reaction vessel dividing portion 8, the DNA amplification reaction and the typing reaction are performed in each of the divided reaction chambers 105, and then measurement is continuously performed. For this reason, since it is not necessary to transfer a sample by using a nozzle, for example, the risk of contamination occurring due to the sample transfer can be eliminated. In addition, since it is not necessary to provide a dispensing mechanism or the like, the apparatus can be made small.

Furthermore, since the reaction container 100 is set and fixed to the movable board 7 in a state where the bottom surface of each reaction vessel 102 is exposed and moves along the rails 12, the reaction vessel dividing portion 8 and the temperature control portion 9 can approach the reaction container 100 from a lower side of the reaction container 100 so that each process can be performed. As a result, since an operation space of the reaction vessel dividing portion 8 and the temperature control portion 9 can be saved, and the configuration of the apparatus can be simplified.

Moreover, since the temperature control portion 9 performs two kinds of temperature controls including a control of a temperature cycle for PCR and heat retention for typing reaction, the determination apparatus 1 can be formed by providing a temperature control mechanism only in one place. As a result, the determination apparatus 1 can be made smaller.

Moreover, in the case of a configuration where the determining portion 23 displays safety information on drugs relevant to the SNP on the display portion 3 together with the determination result, the determination result can be immediately used for daily clinical activity, which contributes to performing medical treatment more suitable to each patient.

Having described the embodiment of the present invention, the technical scope of the present invention is not limited to the above embodiment but various modifications may be made without departing from the spirit and scope of the present invention.

For example, in the above embodiment, the measurement may be performed by an external measuring apparatus without providing the measuring portion.

Furthermore, for example, in the above embodiment, an example where the reaction vessel dividing portion 8 causes the reaction vessel 102 to plastically deform with pressure so that the reaction vessel 102 is divided into the plurality of reaction chambers 105 has been described. However, the determination apparatus of the present invention is not limited thereto. The reaction vessel 102 may be deformed by heating or may be deformed by chemical curing using a temperature change or light beams, such as visible light and ultraviolet rays. In addition, these methods may be suitably combined.

In addition, in the case of adopting the configuration where the reaction vessel 102 deformed by heating, the reaction vessel dividing portion 8 and the temperature control portion 9 may be configured to be united by providing a cooling mechanism in the pressing block 16 of the reaction vessel dividing portion 8. In this case, a transition to the amplification reaction process can be made without moving a reaction container after dividing a reaction vessel into a plurality of reaction chambers. As a result, it becomes possible to make the apparatus smaller and to perform an operation at a higher speed.

In such a configuration, amplification and measurement can be performed while maintaining the division shape of the reaction chamber by the pressing block 16. Accordingly, the reaction container 100 that does not deform plastically can be used.

Furthermore, although an example where the rail 12 is formed in a straight line has been described in the above embodiment, the rail 12 may be suitably curved or meander according to the arrangement of each mechanism. However, since forming the rail 12 in the shape of a straight line makes the distance of the rail 12 shortest, the apparatus can be made simple and small, which is preferable.

Furthermore, instead of forming a track using a rail, the track may also be constituted as follows.

For example, it may be possible to adopt a configuration in which a driving unit (a motor and a wheel, or the like) is provided in the movable board 7 so that the movable board 7 is self-propelled, a guide rail is provided instead of a rail along a side surface of the movable board 7, and for example, a nail stopper is suitably provided at a required position so that the movable board 7 is locked at the required location.

Furthermore, in addition to the track in the present embodiment, an auxiliary track may be constructed over the track (in the air) such that the movable board 7 is held at two points of the track and the auxiliary track in the air.

Alternatively, a driving unit may be provided separately from the movable board 7 with the auxiliary track as a main track instead of the track in the present embodiment and the movable board 7 may suspend and sag from the driving unit such that the reaction container moves to a place, in which various kinds of processing (temperature control, reaction vessel division, and the like) are performed, to perform the processing.

Furthermore, although an example where the reaction container is horizontally disposed and the reaction vessel dividing portion 8 and the temperature control portion 9 approach the reaction container from a lower side of the reaction container has been described, the genetic detection and determination apparatus of the present invention is not limited thereto. For example, upper and lower surfaces of the reaction container may be disposed to be located in the horizontal direction of the determination apparatus 1, such that the reaction vessel dividing portion 8 and the temperature control portion 9 approach the reaction container from the horizontal direction of the determination apparatus 1. In this case, a reaction container temperature control portion 9 performs heating and cooling from one of the upper and lower surface sides of the reaction container or both sides.

Furthermore, in the above embodiment, an example where the temperature control portion 9 performs heating and cooling for amplification and heat retention for the typing reaction has been described. Instead of this, however, the determination apparatus may have a configuration in which the temperature control portion performs the heating and cooling and a temperature control mechanism is provided in the measuring portion such that the typing reaction and the measurement are performed by the measuring portion. In this case, even if the PCR method is not used, it is not necessary to provide the temperature control portion 9 when only a measurable object is set as an object to be measured. As a result, since the number of components can be reduced, the apparatus can be simplified.

Furthermore, in the above embodiment, an example where the emission detecting portion 20 is configured to include optical fibers for excitation light and optical fibers for detection has been described. Instead of this, however, the emission detecting portion may be formed in a box shape by providing an optical system, such as a photoelectric conversion element including an LED for excitation and a photodiode, such that the measurement is performed in a state where a reaction container is accommodated in the emission detecting portion. In this case, since it is not necessary to lead optical fibers, the apparatus can be made small.

Furthermore, in the above embodiment, an example where the set portion 13 of the movable board 7 has a frame shape has been described. Instead of this, however, a U shape may be used, or a configuration in which a reaction container is held in a state interposed from the left and right sides thereof, or a configuration in which a reaction container is held in a state where the peripheral edge of the reaction container is interposed from the upper and lower sides thereof may also be adopted.

In addition, although an example where a reaction container having a reaction vessel is used has been described in the above embodiment, a reaction container having a shape in which individual reaction chambers (wells) are connected through a flow passage may also be used. In this case, the wells may be individually separated from each other by deforming the flow passage portion through the reaction vessel dividing portion, so that the required reactions can be performed therein.

In addition, the temperature control portion 9 may have a configuration of the following incubator in addition to the above-described configuration or instead of the above-described configuration. This incubator will be described with reference to the accompanying drawings.

(Second Embodiment)

Figure 10:
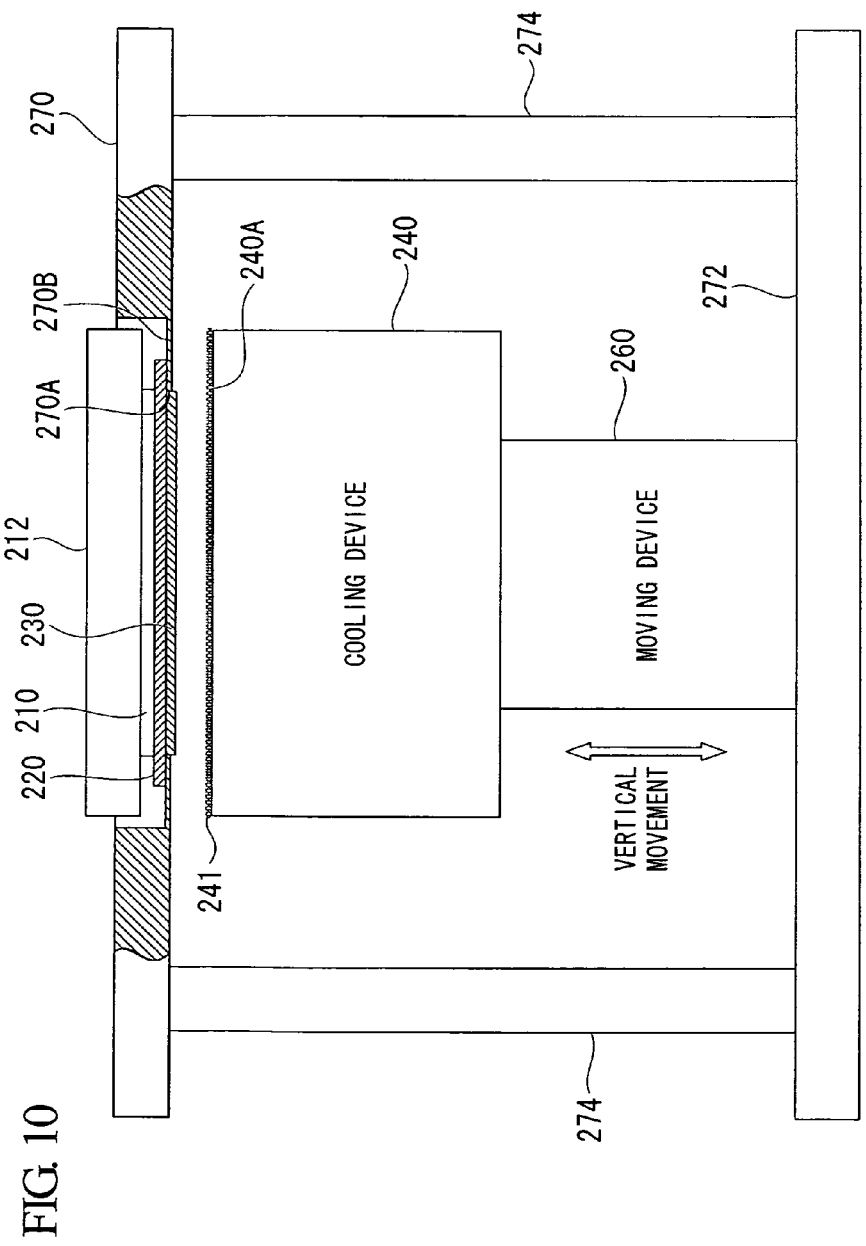
FIG. 10 illustrates the configuration of an incubator according to a second embodiment.

FIG. 10 illustrates the configuration of an incubator according to a second embodiment.

As shown in FIG. 10, in the incubator according to the second embodiment, a reaction sample is received in a DNA chip (container) 210 and the DNA chip 210 is set on a heat transfer block 220 to perform heating and cooling of the DNA chip 210. As a DNA chip, each form of the reaction container in the first embodiment may be used in addition to a known DNA chip. The heat transfer block 220 serves to transfer heat to the DNA chip 210 and is formed of a plate-shaped metal having good thermal conductivity. As the metal, it is preferable to use silver, copper, gold, aluminum, or an alloy including any of them. The heat transfer block 220 is supported by a chip base 270. The chip base 270 has an opening 270A which is smaller than the heat transfer block 220, and a thin recessed portion 270B having a thickness larger than the heat transfer block 220 is provided in the periphery of the opening 270A. The heat transfer block 220 is housed and supported in the recessed portion 270B of the chip base 270. The chip base 270 is supported by several struts 274 fixed to an upper portion of a pedestal 272. On the DNA chip 210, a press 212 for making the DNA chip 210 come in contact with the heat transfer block 220 is provided. The press 212 is formed of a heat insulating material in order to prevent heat dissipation from the DNA chip 210.

A plate-shaped heater 230 passing through the opening 270A of the chip base 270 is provided so as to be in contact with a bottom surface of the heat transfer block 220. The heater 230 serves to heat the heat transfer block 220. It is preferable that the heater 230 be heated and cooled quickly. For example, the heater 230 is a ceramic heater with high thermal conductivity. As a ceramic material, it is preferable to use an aluminum nitride, an aluminum oxide, a silicon carbide, a silicon nitride, or the like.

A cooling device 240 is provided below the heater 230. The cooling device 240 is provided to be movable between a contact position being in contact with the heater 230 and a distant position separated from the heater 230 and comes in contact with the heater 230 at the contact position to cool the heat transfer block 220. A moving device 260 which is provided on the pedestal 272, supports the cooling device 240, and moves the cooling device 240 to the contact position and the distant position is provided below the cooling device 240. The cooling device 240 has a contact surface 240A being in contact with a bottom surface of the heater 230, and a thermally conductive sheet 241 which is bonded to the contact surface 240A. In this way, the thermal contact resistance can be reduced.

According to the second embodiment, when a reaction sample is heated, the heat transfer block 220 that holds the DNA chip 210, in which reaction samples are accommodated, is quickly heated by the heater 230 provided in contact with the heat transfer block 220. On the other hand, when a reaction sample is cooled, the cooling device 240 comes in contact with the heater 230 such that the heat transfer block 220 is immediately cooled through the heater 230 by the cooling device 240. Since the heater 230 is a ceramic heater with high thermal conductivity, the heater 230 is quickly cooled when the cooling device 240 comes in contact with the heater 230. Thus, the temperature of a reaction sample can be controlled rapidly by quickly heating or cooling the reaction sample.

In addition, the preset temperature of the heater 230 does not necessarily need to be set to a target temperature. For example, heating can be performed at a higher speed by setting the preset temperature of the heater 230 to a temperature higher than the target temperature at first and gradually lowering the preset temperature to the target temperature. The same is true for the cooling device.

In addition, only the moving device 260 which moves the cooling device 240 to the contact position and the distant position operates. Accordingly, it is possible to simplify the configuration of the apparatus and it becomes easy to make the apparatus small.

In addition, the heater 230, the cooling device 240, and the moving device 260 are provided below the heat transfer block 220 which holds the DNA chip 210. For this reason, since room in a space is secured above the DNA chip 210, setting of the DNA chip 210, measurement such as fluorescence detection, and the like become easy. As a result, an apparatus having good operability can be provided.

(Third Embodiment)

Figure 11:
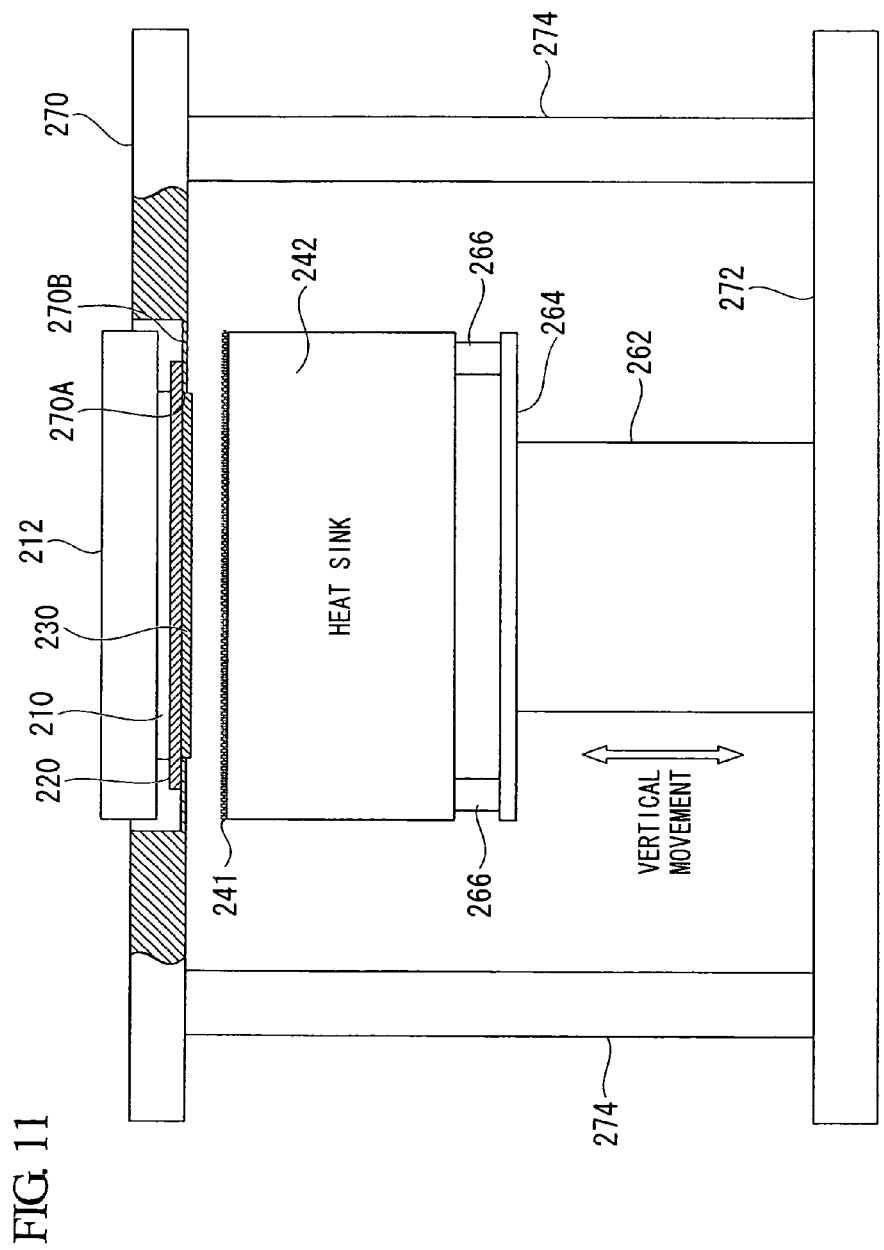
FIG. 11 illustrates the configuration of an incubator according to a third embodiment.

FIG. 11 illustrates the configuration of an incubator according to a third embodiment.

As shown in FIG. 11, in the incubator according to the third embodiment, a heat sink 242 is used as the cooling device 240 in the second embodiment and an air cylinder 262 is used as the moving device 260 in the second embodiment. The heat sink 242 is fixed to a stationary plate 264 of the air cylinder 262 with spacers 266 interposed therebetween. A thermally conductive sheet 241 is bonded to an upper surface of the heat sink 242. When a reaction sample is cooled, the heat sink 242 comes in contact with the heater 230 so that heat is dissipated from the heater 230. The heat sink is formed of a metal selected from aluminum, an aluminum alloy, and copper.

In addition, since other portions have the same configurations as those in the incubator according to the second embodiment, the same reference numerals are given and an explanation thereof will be omitted.

According to the third embodiment, since the heat sink 242 is used as the cooling device 240, the configuration of the apparatus is most simple. In addition, since the air cylinder 262 is used as the moving device 260, the configuration of the apparatus becomes simple.

In addition, although examples of using the air cylinder 262 will be described in the following embodiments, the moving device 260 is not limited to the air cylinder 262. For example, one with a simple configuration, such as one obtained by combining an electromagnetic actuator (solenoid), a spring, and a motor or one obtained by combining a motor and a screw may preferably be used.

(Fourth Embodiment)

Figure 12:
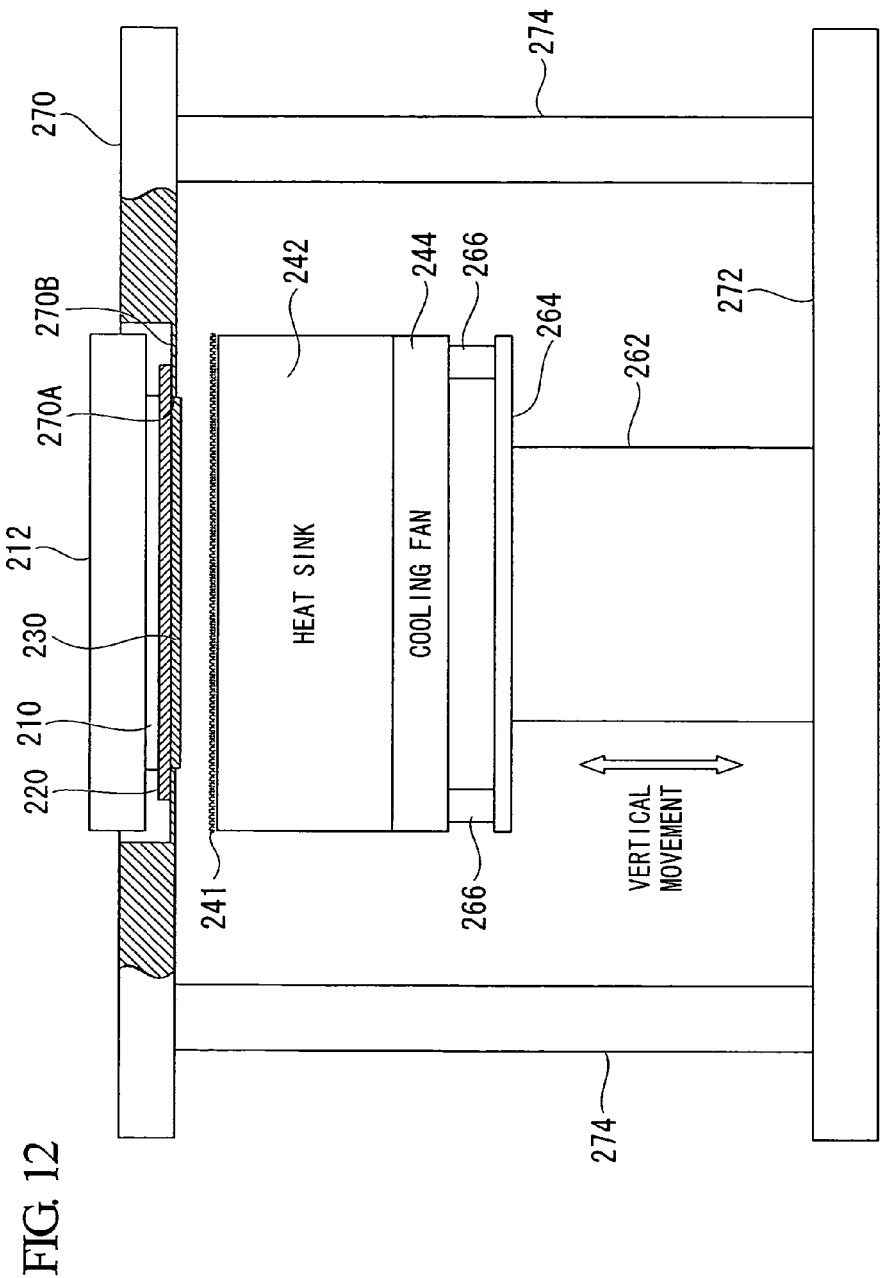
FIG. 12 illustrates the configuration of an incubator according to a fourth embodiment.

FIG. 12 illustrates the configuration of an incubator according to a fourth embodiment.

As shown in FIG. 12, in the incubator according to the fourth embodiment, a cooling fan 244 which cools the heat sink 242 is provided below the heat sink 242 of the incubator according to the third embodiment. The heat sink 242 and the cooling fan 244 are fixed to a stationary plate 264 of an air cylinder 262 with spacers 266 interposed therebetween.

In addition, since other portions have the same configurations as those in the incubator according to the third embodiment, the same reference numerals are given and an explanation thereof will be omitted.

Since the heat sink 242 serves to only dissipate heat, there is a problem in that when the heat sink 242 is used as a single body, the temperature of the heat sink 242 rises due to repetition of heating and cooling and accordingly, the cooling speed is lowered.

In contrast, according to the third embodiment, the cooling fan 244 which cools the heat sink 242 is provided. Accordingly, even if heating and cooling are repeated, the temperature of the heat sink 242 can be kept constant. As a result, rapid cooling can be realized until the PCR reaction is completed.

(Fifth Embodiment)

Figure 13:
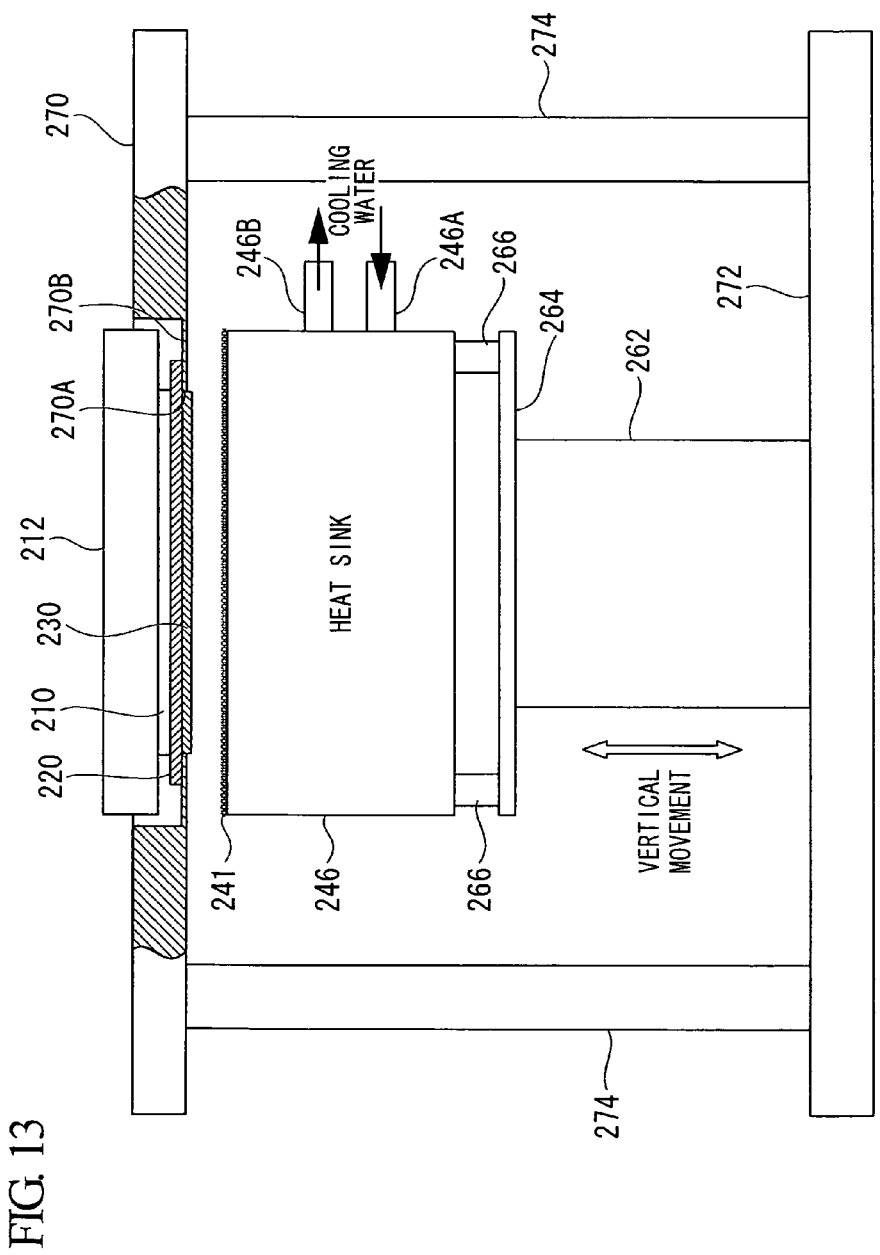
FIG. 13 illustrates the configuration of an incubator according to a fifth embodiment.

FIG. 13 illustrates the configuration of an incubator according to a fifth embodiment.

As shown in FIG. 13, the incubator according to the fifth embodiment includes a heat sink 246 that is fixed to a stationary plate 264 of an air cylinder 262 with spacers 266 interposed therebetween. A pipeline (not shown) through which a fluid flows is provided in the heat sink 246, such that cooling water circulates through the pipeline to cool the heat sink 246.

A water inlet 246A used to supply cooling water and a water outlet 246B used to discharge cooling water are provided in the heat sink 246. A thermally conductive sheet 241 is bonded to an upper surface of the heat sink 246.

In addition, since other portions have the same configurations as those in the incubator according to the third embodiment, the same reference numerals are given and an explanation thereof will be omitted.

According to the fifth embodiment, since the heat sink 246 is cooled by cooling water that circulates, the temperature of the heat sink 246 can be kept constant even if heating and cooling are repeated. As a result, rapid cooling can be realized until the PCR reaction is completed.

In addition, since the thickness of the heat sink 246 in the vertical direction can be made small compared with the heat sink 242 in the third embodiment, the apparatus can be miniaturized.

(Sixth Embodiment)

Figure 14:
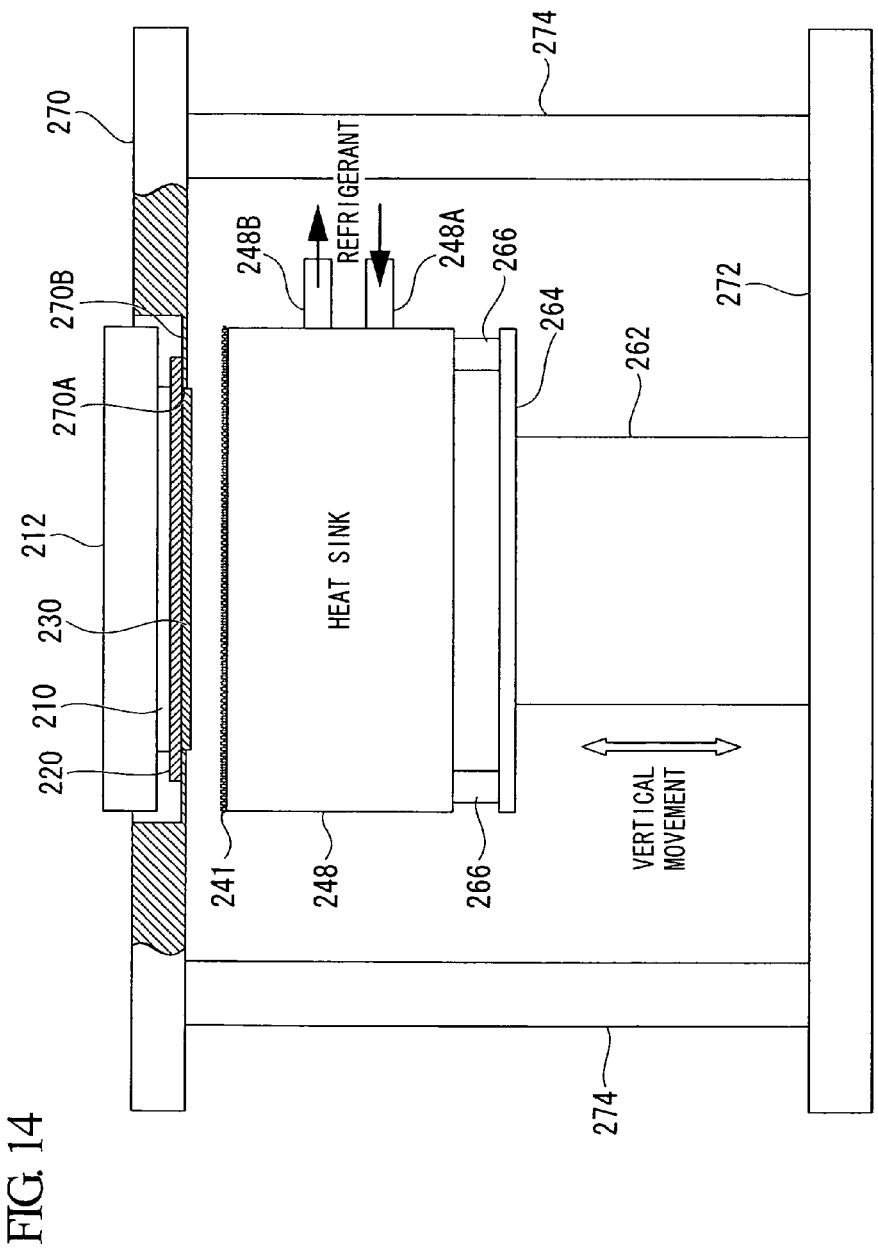
FIG. 14 illustrates the configuration of an incubator according to a sixth embodiment.

FIG. 14 illustrates the configuration of an incubator according to a sixth embodiment.

As shown in FIG. 14, the incubator according to the sixth embodiment includes a heat sink 248 that is fixed to a stationary plate 264 of an air cylinder 262 with spacers 266 interposed therebetween. A pipeline (not shown) through which a fluid flows is provided in the heat sink 248, such that refrigerant having a lower boiling point than the target cooling temperature circulates through the pipeline to cool the heat sink 248 by the vaporization. A supply port 248A used to supply the refrigerant and a discharge port 248B used to discharge the refrigerant are provided in the heat sink 248. A thermally conductive sheet 241 is bonded to an upper surface of the heat sink 248. Examples of the refrigerant may include ethyl alcohol, diethyl ether, benzene, ammonia, acetylene, liquid nitrogen, and the like.

In addition, since other portions have the same configurations as those in the incubator according to the third embodiment, the same reference numerals are used and an explanation thereof will be omitted.

According to the sixth embodiment, since the heat sink 248 is cooled by the refrigerant that circulates, the temperature of the heat sink 248 can be kept constant even if heating and cooling are repeated. As a result, rapid cooling can be realized until the PCR reaction is completed.

In addition, since the thickness of the heat sink 248 in the vertical direction can be made small compared with the heat sink 242 in the third embodiment, the apparatus can be miniaturized.

(Seventh Embodiment)

Figure 15:
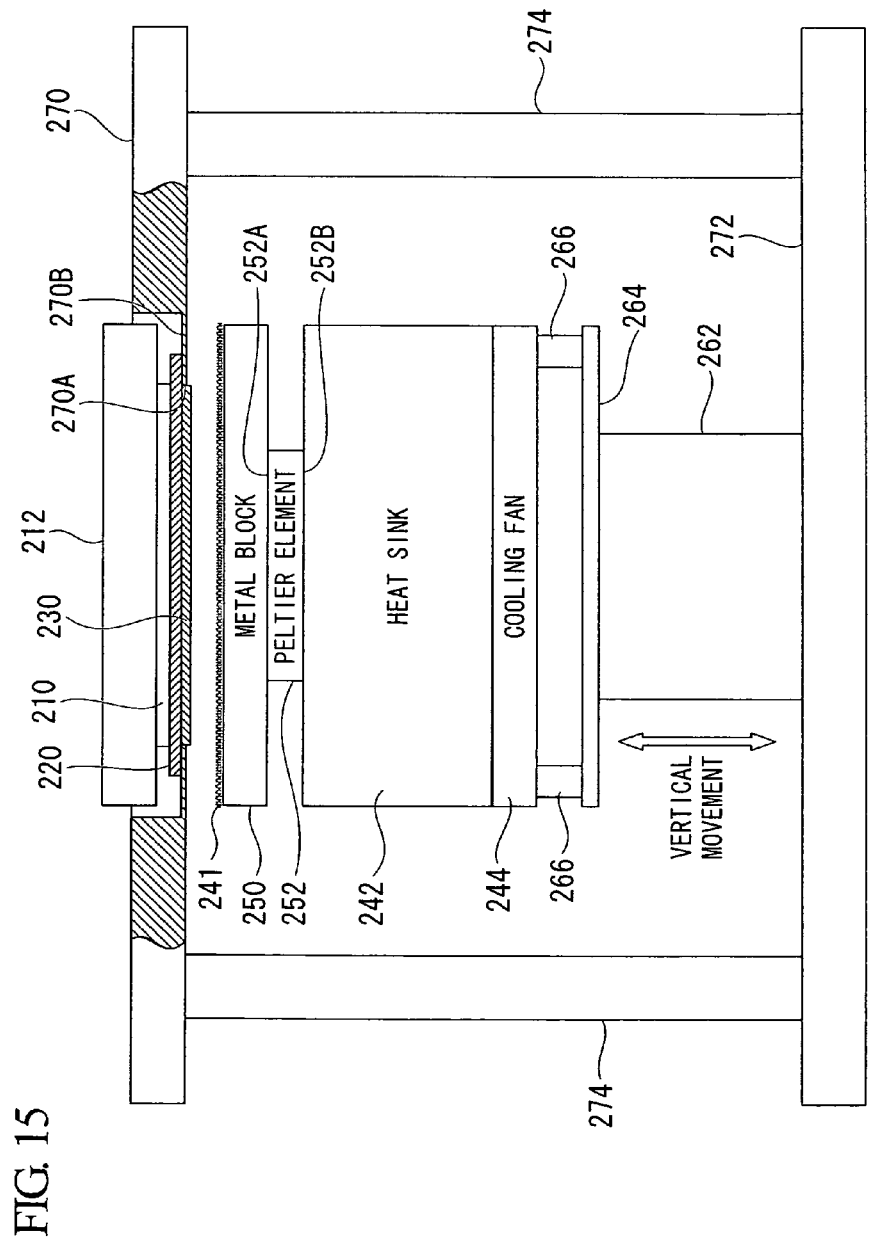
FIG. 15 illustrates the configuration of an incubator according to a seventh embodiment.

FIG. 15 illustrates the configuration of an incubator according to a seventh embodiment.

As shown in FIG. 15, the incubator according to the seventh embodiment includes a metal block 250, which cools a heater 230, and a Peltier element 252 provided on a bottom surface of the metal block 250 so as to be in contact with the metal block 250.

The metal block 250 is formed of a metal having good thermal conductivity, for example, silver, copper, gold, or aluminum. A thermally conductive sheet 241 is bonded to an upper surface of the metal block 250.

The Peltier element 252 cools the heater 230 to a predetermined temperature through the metal block 250. The Peltier element 252 has an heat absorbing surface 252A and a heat dissipating surface 252B, and absorbs (cools) heat through the heat absorbing surface 252A as well as dissipates heat through the heat dissipating surface 252B. The heat absorbing surface 252A is in contact with the bottom surface of the metal block 250.

A heat sink 242 for cooling the heat dissipated from the heat dissipating surface 252B of the Peltier element 252 is provided on the heat dissipating surface 252B of the Peltier element 252 so as to be in contact with the heat dissipating surface 252B, and a cooling fan 244 which cools the heat sink 242 is provided below the heat sink 242.

The heat sink 242 and the cooling fan 244 are fixed to a stationary plate 264 of an air cylinder 262 with spacers 266 interposed therebetween.

In addition, since other portions have the same configurations as those in the incubator according to the third embodiment, the same reference numerals are given and an explanation thereof will be omitted.

According to the seventh embodiment, since the cooling temperature can be arbitrarily set by the Peltier element 252, the cooling speed can be controlled more precisely. For example, since the cooling temperature can be set less than or equal to the room temperature by the Peltier element 252, a further rapid cooling can be realized.

(Eighth Embodiment)

In the eighth embodiment, the following incubator may be provided instead of the temperature control portion 9 of the determination apparatus 1 according to the first embodiment.

Figure 16:
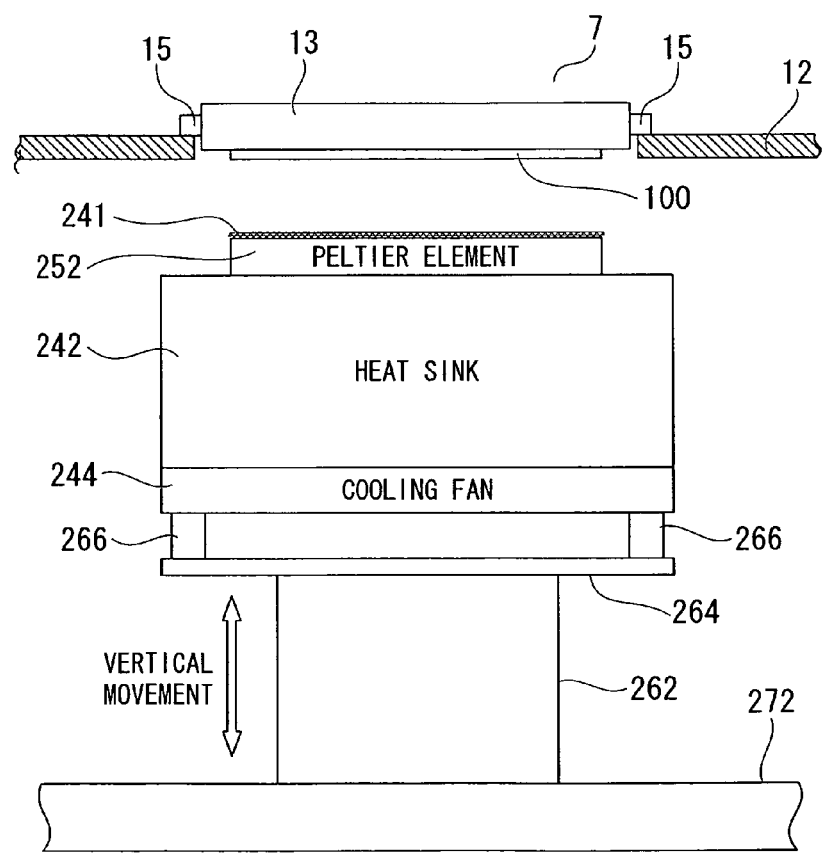
FIG. 16 illustrates the configuration of an incubator according to an eighth embodiment.

FIG. 16 illustrates the configuration of a determination apparatus 1 according to the eighth embodiment.

The incubator according to the eighth embodiment includes a Peltier element 252. The Peltier element 252 of the incubator is disposed below a movable board (container set portion) 7.

The Peltier element 252 has an heat absorbing surface 252A and a heat dissipating surface 252B, and absorbs (cools) heat through the heat absorbing surface 252A and dissipates heat through the heat dissipating surface 252B.

Since the Peltier element 252 can switch between functions of the heat absorbing surface 252A and the heat dissipating surface 252B, heating and cooling can be performed by one Peltier element 252.

A heat sink 242 for cooling the heat dissipated from the heat dissipating surface 252B of the Peltier element 252 is provided on the heat dissipating surface 252B of the Peltier element 252 so as to be in contact with the heat dissipating surface 252B, and a cooling fan 244 which cools the heat sink 242 is provided below the heat sink 242. A thermally conductive sheet 241 is bonded to an upper surface of the Peltier element 252.

The heat sink 242 and the cooling fan 244 are fixed to a stationary plate 264 of an air cylinder 262 with spacers 266 interposed therebetween.

In addition, since the configurations of the spacer 266, the air cylinder 262, and the stationary plate 264 are the same as those in the incubator according to the third embodiment, the same reference numerals are given and an explanation thereof will be omitted.

According to the eighth embodiment, since the cooling temperature can be arbitrarily set by the Peltier element 252, the cooling speed can be controlled more precisely. For example, since the cooling temperature can be set to be less than or equal to the room temperature by the Peltier element 252, a further rapid cooling can be realized.

In addition, according to the eighth embodiment, since a reaction vessel is deformed to be divided into a plurality of reaction chambers and rapid and precise heating and cooling are performed by the incubator, most of the detection and determination operations can be mechanized. As a result, since human errors are prevented, many samples can be processed efficiently.

In addition, according to the eighth embodiment, it becomes possible to shorten the time taken to perform genetic detection and determination and to provide a small apparatus.

That is, it is possible to make the apparatus small by placing a heating and cooling mechanism and a detection mechanism around a movable board which moves along the rails.

Rapidly heating and cooling and miniaturization can be simultaneously realized by constructing the heating and cooling mechanism of the embodiments of the present invention, in contrast with the larger conventional heating and cooling mechanism.

(Industrial Applicability)

According to the genetic detection and determination apparatus of the present invention, the genetic detection and determination apparatus which is small and in which human error or contamination rarely occurs can be provided.

Furthermore, according to the genetic detection and determination method of the present invention, the genetic determination can be performed while suppressing human error or contamination.

Furthermore, according to the incubator of the present invention, miniaturization becomes easy with a simple configuration and the PCR reaction time can be shortened by controlling the temperature of a reaction sample rapidly.

The invention claimed is:

1. A genetic detection and determination apparatus which detects or determines genetic information, comprising:
    a reaction container in which a plurality of grooved reaction vessels are disposed so as to be aligned approximately in parallel to each other;
    a container set portion on which the reaction container is set;
    a moving mechanism which moves the container set portion along a track;
    a reaction vessel dividing portion including
        an arch portion having a flat top plate, and
        a pressing block provided on the track and below the arch portion, capable of moving in a vertical direction, and including a plurality of protruding portions formed on one common member which is the pressing block, the protruding portions configured to simultaneously move up due to upward movement of the pressing block while the reaction vessels are between the protruding portions and the top plate, thereby dividing the reaction vessels into a plurality of independent reaction chambers by deforming the reaction vessels;
    a temperature control portion
        provided on the track at a location spaced apart from the reaction vessel dividing portion by a predetermined distance,
        comprising a heating portion and a cooling portion provided below the heating portion,
        movable in the vertical direction, and
        configured to move up toward the container set portion after the container set portion moves to an upper area of the temperature control portion and stops, the temperature control portion thereby coming in contact with a bottom surface of each of the reaction vessels, thereby heating and cooling the reaction container by coming in contact with the bottom surface of each reaction vessel; and
    a measuring portion which is movable above the container set portion in parallel to an upper surface of the reaction container provided on the container set portion and which measures a reaction within each of the reaction chambers, wherein
        the container set portion is configured to move to an upper area of the reaction vessel dividing portion and the upper area of the temperature control portion along a rail.

2. The genetic detection and determination apparatus according to claim 1, wherein the reaction vessel dividing portion divides the reaction vessel by plastic deformation.

3. The genetic detection and determination apparatus according to claim 1, further comprising:
    a determining portion which detects or determines the genetic information based on a measurement value of the measuring portion and searches and acquires related information relevant to a determination result from a database; and
    a display portion that displays the determination result of the determining portion and the related information.

4. The genetic detection and determination apparatus according to claim 1, further comprising:
    a reader portion which reads information from an information recording portion which is included in the reaction container.

5. A genetic detection and determination method of detecting or determining predetermined genetic information, comprising:
    adding a sample containing a genetic material in a plurality of grooved reaction vessels disposed in the reaction container so as to be aligned approximately in parallel to each other;
    executing a reaction vessel dividing process using a pressing block capable of moving in a vertical direction and an arch portion provided the pressing block, the pressing block including a plurality of protruding portions formed on one common member which is the pressing block, the arch portion including a flat top plate, and the dividing process performed by having the protruding portions simultaneously move up toward the reaction container due to upward movement of the pressing block while the reaction vessel is between the protruding portions and the top plate, thereby forming a plurality of independent reaction chambers in the reaction container by deforming the reaction vessels;
    executing an amplification reaction process which performs an amplification and a typing reaction of the genetic material within the sample by moving the container set portion to an upper area of a temperature control portion, stopping the container set portion at the upper area of a temperature control portion, and allowing the temperature control portion to move up toward the reaction container to come in contact with a bottom surface of the reaction container, thereby performing at least one of heating and cooling of the reaction container from the bottom surface of the reaction container;
    executing a measuring process which measures a result of the reaction within each of the reaction chambers from above the reaction container during or after the amplification reaction process; and
    detecting or determining the genetic information based on a measurement value obtained in the measuring process.

6. The genetic detection and determination apparatus according to claim 1,
    wherein the reaction vessel has:
    a plurality of reaction sub-rooms; and
    a flow passage that connects the plurality of reaction sub-rooms, and
    wherein the reaction vessel dividing portion deforms the flow passage of the reaction vessel, and thereby divides the reaction vessel so that the plurality of reaction sub-rooms becomes the plurality of reaction chambers.

7. A genetic reactor which detects or determines genetic information, comprising:
a reaction container in which a plurality of grooved reaction vessels are disposed so as to be aligned approximately in parallel to each other;
a container set portion on which the reaction container is set;
a moving mechanism which moves the container set portion along a track;
a reaction vessel dividing portion including
an arch portion having a flat top plate, and
a pressing block provided on the track and below the arch portion, capable of moving in a vertical direction, and including a plurality of protruding portions formed on one common member which is the pressing block, the protruding portions configured to simultaneously move up due to upward movement of the pressing block while the reaction vessels are between the protruding portions and the top plate, thereby dividing the reaction vessels into a plurality of independent reaction chambers by deforming the reaction vessels; and
a temperature control portion
provided on the track at a location spaced apart from the reaction vessel dividing portion by a predetermined distance,
comprising a heating portion and a cooling portion provided below the heating portion,
movable in the vertical direction, and
configured to move up toward the container set portion after the container set portion moves to an upper area of the temperature control portion and stops, the temperature control portion thereby coming in contact with a bottom surface of each of the reaction vessels, thereby heating and cooling the reaction container by coming in contact with the bottom surface of each reaction vessel, wherein
the container set portion is configured to move to an upper area of the reaction vessel dividing portion and the upper area of the temperature control portion along a rail.

8. An incubator comprising:
a container in which a reaction sample is accommodated;
a heat-conductive heat transfer block on which the container is set and which holds the container;
a heater which is in contact with a bottom surface of the heat transfer block and heats the heat transfer block;
a cooling device which is movable vertically between a contact position being in contact with the heater and a distant position separated from the heater, and which comes in contact with a bottom surface of the heater at the contact position by moving up towards the heater from the distant position to cool the heat transfer block;
a pedestal; and
a moving device which moves the cooling device to the contact position and the distant position and supports the cooling device, the moving device being provided on the pedestal and below the cooling device.

9. The incubator according to claim 8, wherein
the heater is in contact with a bottom surface of the heat transfer block,
the cooling device is in contact with a bottom surface of the heater at the contact position, and
the moving device supports the cooling device from at least one of the downward and lateral directions thereof.

10. The incubator according to claim 8, wherein the moving device includes an air cylinder.

11. The incubator according to claim 8, wherein the moving device includes an electromagnetic actuator.

12. The incubator according to claim 8, wherein the heat transfer block includes a heat-conductive material.

13. The incubator according to claim 8, wherein the heater includes a ceramic material with high thermal conductivity.

14. The incubator according to claim 13,
wherein the ceramic material contains aluminum nitride, aluminum oxide, silicon carbide, or silicon nitride.

15. The incubator according to claim 8, wherein the cooling device has a contact surface that comes in contact with a bottom surface of the heater at the contact position by moving up towards the heater when the cooling device moves from the distant position to cool the heat transfer block, and
a thermally conductive sheet which is provided at the contact surface.

16. The incubator according to claim 8, wherein the cooling device includes a heat sink which is movable vertically and which moves up toward the heater when the cooling device moves up from the distant position.

17. The incubator according to claim 16, wherein
the heat sink has a pipeline through which a fluid flows, and
the heat sink is cooled by cooling water which flows to circulate through the pipeline.

18. The incubator according to claim 16, wherein
the heat sink has a pipeline through which a fluid flows, and
the heat sink is cooled by a refrigerant which flows to circulate through the pipeline and has a lower boiling point than a predetermined cooling temperature.

19. The incubator according to claim 8, wherein the cooling device has a heat sink and a fan which cools the heat sink.

20. The incubator according to claim 8, wherein the cooling device includes:
a metal block which transfers heat to the heater;
a Peltier element which has a heat absorbing surface which absorbs heat and a heat dissipating surface dissipates heat, the heat absorbing surface being in contact with the metal block;
a heat sink being in contact with the heat dissipating surface of the Peltier element; and
a fan which cools the heat sink.

21. The incubator according to claim 20, wherein the metal block includes a heat-conductive material.

22. The incubator according to claim 8, wherein the cooling device includes:
a Peltier element which has a heat absorbing surface which absorbs heat and a heat dissipating surface dissipates heat;
a heat sink being in contact with the heat dissipating surface of the Peltier element; and
a fan which cools the heat sink.

23. A genetic detection and determination apparatus which detects or determines genetic information provided with a reaction container having a reaction vessel, comprising:
the incubator according to claim 8;
a container set portion on which the reaction container is set;
a moving mechanism which moves the container set portion along a track;
a reaction vessel dividing portion which divides the reaction vessel into a plurality of reaction chambers by deforming the reaction vessel; and
a measuring portion which is movable above the container set portion in parallel to an upper surface of the reaction container provided on the container set portion and which measures reaction within each of the reaction chambers.

24. The incubator according to claim 20, wherein each of the Peltier element, the heat sink and the fan is movable vertically and moves up toward the heater when the cooling device moves up from the distant position.

\* \* \* \* \*